US008663655B2

(12) United States Patent
Boyaval et al.

(10) Patent No.: US 8,663,655 B2
(45) Date of Patent: Mar. 4, 2014

(54) **METHOD FOR TRANSFORMING A BACTERIUM BELONGING TO THE *STREPTOCOCCUS* GENUS BY NATURAL COMPETENCE**

(75) Inventors: Patrick Boyaval, La Mézière (FR); Christophe Fremaux, Potiers (FR); Pascal Hols, Vedrin (BE); Laetitia Fontaine, Louvain-la-Neuve (BE); Philippe Horvath, St-Gervais-les-Trois-Clochers (FR)

(73) Assignee: Dupont Nutrition Biosciences APS, Copenhagen (DK)

( * ) Notice: Subject to any disclaimer, the term of this patent is extended or adjusted under 35 U.S.C. 154(b) by 0 days.

(21) Appl. No.: 13/380,273

(22) PCT Filed: Jun. 23, 2010

(86) PCT No.: PCT/EP2010/058947
§ 371 (c)(1),
(2), (4) Date: Dec. 22, 2011

(87) PCT Pub. No.: WO2010/149721
PCT Pub. Date: Dec. 29, 2010

(65) Prior Publication Data
US 2012/0129264 A1    May 24, 2012

Related U.S. Application Data

(60) Provisional application No. 61/219,436, filed on Jun. 23, 2009, provisional application No. 61/239,896, filed on Sep. 4, 2009.

(51) Int. Cl.
*A61K 39/09* (2006.01)
*C07K 14/195* (2006.01)

(52) U.S. Cl.
USPC .................... 424/244.1; 424/190.1; 530/300; 435/810; 435/975

(58) Field of Classification Search
None
See application file for complete search history.

(56) References Cited

U.S. PATENT DOCUMENTS

| 7,393,663 B2 * | 7/2008 | Edwards et al. ............. 435/69.8 |
| 2005/0136404 A1 | 6/2005 | Doucette-Stamm |
| 2009/0144848 A1 | 6/2009 | Kovalic |

FOREIGN PATENT DOCUMENTS

| EP | 2248823 A1 | 11/2010 |
| WO | WO 2007129072 A2 | 11/2007 |
| WO | WO 2010125091 A1 | 11/2010 |

OTHER PUBLICATIONS

International Preliminary Report on Patentability and Written Opinion of the International Searching Authority dated Jan. 4, 2012 for PCT/EP2010/058947.

Bachmann H et al., High-throughput identification and validation of in situ-expressed genes of *Lactococcus lactis*, Applied Environmental Microbiology, 2008, vol. 74, p. 4727-4736.
Barbe V et al., "Unique features revealed by the genome sequence of *Acinetobacter* sp. ADPI, a versatile and naturally transformation competent bacterium", Nucleic Acids Research, 2004, vol. 32, No. 19, p. 5766-5779 XP002336521.
Blomqvist T, et al., Natural genetic transformation: a novel tool for efficient genetic engineering of the dairy bacterium *Streptococcus thermophilus*, Applied Environmental Microbiology, 2006, vol. 72, p. 6751-6756.
Bolotin et al., Complete sequence and comparative genome analysis of the dairy bacterium *Streptococcus thermophilus*, Nat. Biotechnology., 2004, vol. 22, p. 1554-1558.
Claverys JP et al., Bacterial "competence" genes: signatures of active transformation, or only remnants?, Trends Microbiol., 2003, vol. 11, p. 161-165.
Claverys JP et al., Induction of competence regulons as a general responses to stress in gram-positive bacteria, Annu. Rev. Microbiol., 2006, vol. 60, p. 451-475.
Database UniProt accession No. Q6FB69, Jul. 19, 2004.
Eddy S R, Where did he BLOSUM62 alignment score matrix come from?, Nature Biotechnology, 2004, vol. 22, p. 1035-1036.
Fernandez-Espla MD et al., *Streptococcus thermophilus* cell all-anchored proteinase: release, purification, and biochemical and genetic characterization, Applied Environ. Microbiol., 2000, vol. 66, p. 4772-4778.
Fontaine L et al., "A novel pherome quorum-sensing system controls the development of natural competence in *Streptococcus thermophilus* and *Streptococcus salivarius*", Journal of Bacteriology, 2001 vol. 192, No. 5, p. 1444-1454 XP002595773.
Fontaine L et al., Quorum sensing regulation of the production of Bpl bacteriocins in *Streptococcus thermophilus*, J Bacteriol., 2007, vol. 189, p. 7195-7205.
Gardan R. et al., "The Oligopeptide Transport System is essential for the development of natural competence in *Streptococcus thermophilus* Strain LMD-9", Journal of Bacteriology, 2009, vol. 191, No. 14, p. 4647-4655 XP009121572.
Hols et al., "New insights in the molecular biology and physiology of *Streptococcus thermophilus* revealed by comparative genomics", FEMS Microbiology Review, 2005, vol. 29, No. 3, p. 435-463 XP005041538.
Huggins AR et al., Differentiation of fast and slow milk-coagulating isolates in strains of lactic *Streptococci*, J Dairy Science, 1984, vol. 67, p. 1674-1679.
Ibrahim M et al., Control of the transcription of a short gene encoding a cyclic peptide in *Streptococcus thermophilus*: a new quorum-sensing system?, J Bacteriol., 2007, vol. 189, p. 8844-8854.
Knutsen E. et al., "Two separate quorum-sensing systems upregulate transcription of the same ABC transporter in *Streptococcus pneumoniae*", Journal of Bacteriology, 2004, vol. 186, No. 10, p. 3078-3085 XP0025500676.
Kozlowicz B K et al., Molecular basis for control of conjugation by bacterial pheromone and inhibitor peptides, Mol. Microbiol., 2006, vol. 62, p. 958-869.
Lambert J M et al., Cre-lox-based system for multiple gene deletions and selectable-marker removal in *Lactobacillus plantarum*, Appl. Environ. Microbiol. 73, p. 1126-1135, 2007.

(Continued)

*Primary Examiner* — Padma V Baskar
(74) *Attorney, Agent, or Firm* — Steptoe & Johnson LLP

(57) ABSTRACT

The present invention relates to peptides, nucleic acids and methods for transforming a bacterium belonging to the *Streptococcus* genus by natural competence and their use in the food and feed industry.

41 Claims, 12 Drawing Sheets

(56) References Cited

OTHER PUBLICATIONS

Figure 1:
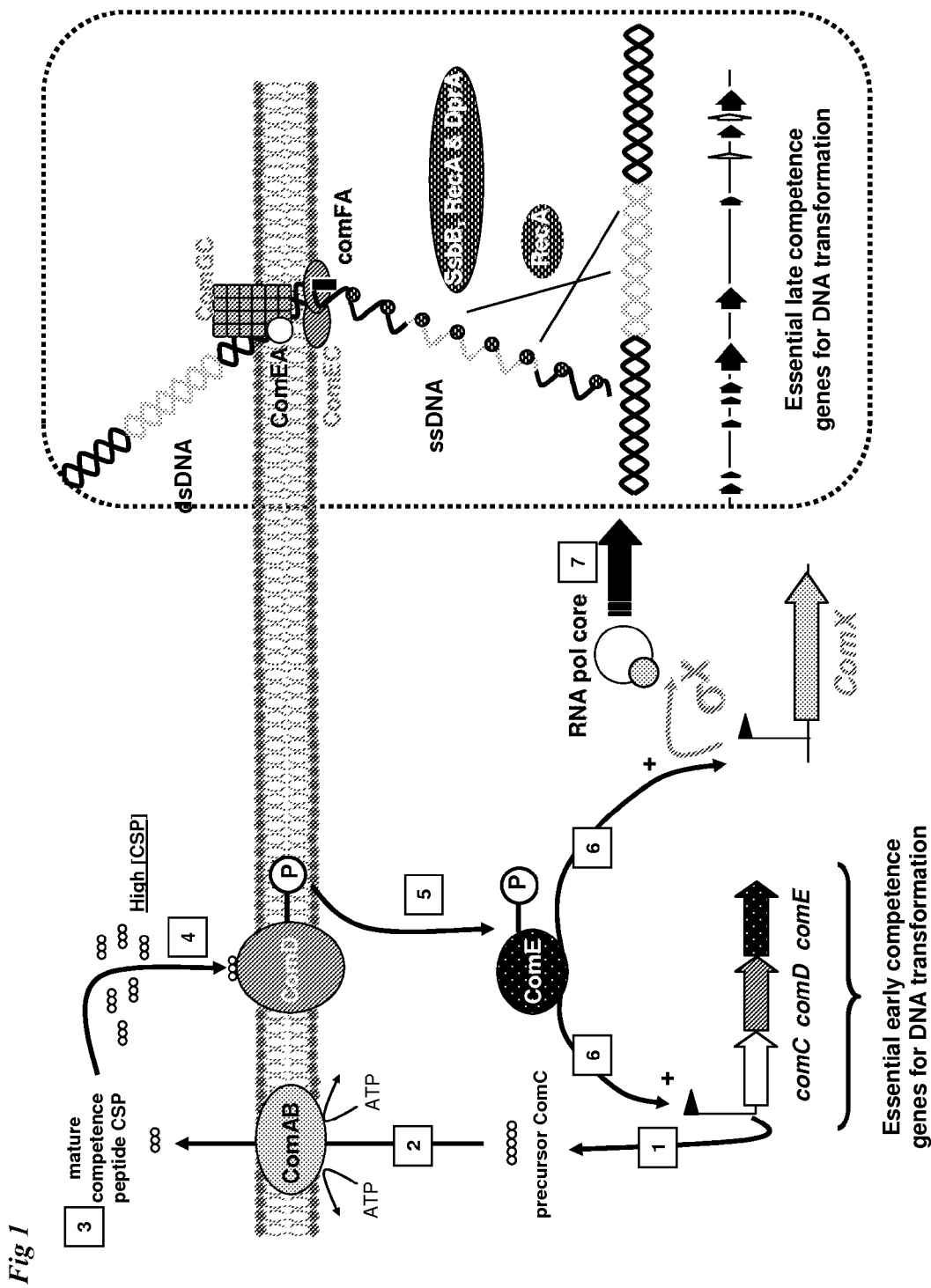

Maguin E et al., Efficient insertional mutagenesis in *Lactococci* and other gram-positive bacteria, Journal of Bacteriology, 1996, vol. 178, p. 931-935.

Maguin E et al., New thermosensitive plasmid for gram-positive bacteria, Journal of Bacteriology, 1992, vol. 174, p. 5633-5638.

Makarova et al., Comparative genomics of the lactic acid bacteria, Proc Natl. Acad. Sci USA, 2006, vol. 103, p. 15611-15616.

Martin B et al., Independent evolution of competence regulatory cascades in *Streptococci*? Trends Microbiol., 2006, 14, p. 339-345.

Slamti L et al., A cell-cell signaling peptide activates the PlcR virulence regulon in bacteria of *Bacillus cereus* group, EMBO J., 2002, vol. 21, p. 4550-4559.

Spinnler H E et al., Automatic method to quantify starter activity based on pH measurement, J Dairy Research, 1989, vol. 56, p. 755-764.

International Search Report and the Written Opinion of the International Searching Authority dated Aug. 23, 2010 for PCT/EP2010/058947.

* cited by examiner

*Fig 9*
A) LMD-9 (His⁺)
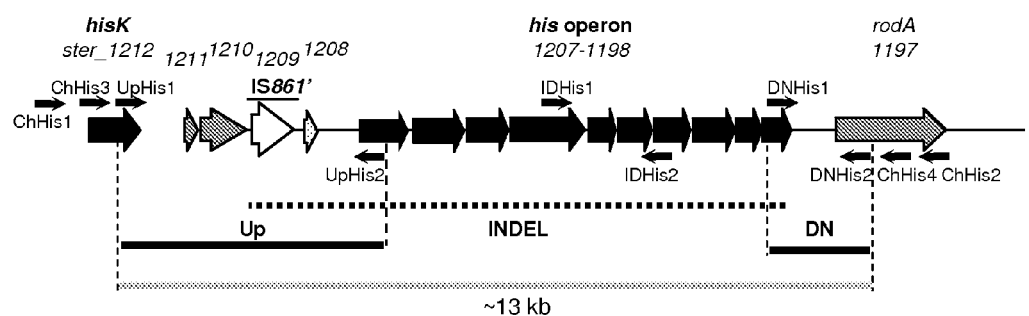
B) LMG 18311 (His⁻)
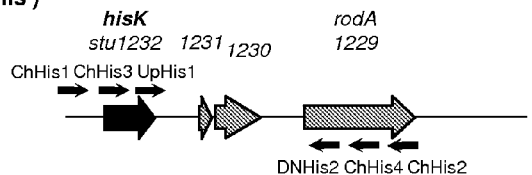

METHOD FOR TRANSFORMING A BACTERIUM BELONGING TO THE *STREPTOCOCCUS* GENUS BY NATURAL COMPETENCE

CLAIM FOR PRIORITY

This application claims priority under 35 USC 371 to International Application No. PCT/EP2010/058947, filed on Jun. 23, 2010, which claims priority to U.S. Application No. 61/219,436, filed Jun. 23, 2009, and U.S. Application No. 61/239,896, filed Sep. 4, 2009, each of which is hereby incorporated by reference in its entirety.

FIELD OF THE INVENTION

The present invention relates to a method for transforming a bacterium belonging to the *Streptococcus* genus by natural competence.

BACKGROUND OF THE INVENTION

*Streptococcus thermophilus* is widely used for the manufacture of yoghurt and Swiss or Italian-type cheeses. These products have a market value of approximately $40 billion per year, making *S. thermophilus* a species that has major economic importance. Even though the fermentation properties of this bacterium have been gradually improved by selection and classical methods, there is great potential for further improvement through natural processes or by genetic engineering. To be able to improve naturally, without any genetic engineering technology involved, *S. thermophilus* technological performances, physiological properties, behaviour in different growth media is of key importance for fermented food and feed industries. The obtained improved strains of *S. thermophilus* will be in total compliance with all current regulations concerning living microorganisms for food and feed.

In silico analyses of the currently available *S. thermophilus* genome sequences suggest that many genes were acquired through horizontal gene transfer (1). These horizontal gene transfers potentially occurred through natural transformation designated as competence, as reported in pathogenic streptococci that use competence as a general mechanism for genomic plasticity.

Competence is the ability of a cell to take up extracellular ("naked") DNA from its environment and to integrate this DNA (or part thereof) in its genome. Competence can be separated into natural competence and artificial competence. Natural competence is a genetically specified ability of bacterial strain to perform this DNA uptake. It is thought to occur spontaneously in natural environment and is observed as well in laboratory conditions. Natural competence seems to be a common trait among streptococci (2, 3). By contrast, artificial competence is provoked in laboratory conditions and consists of rendering the cells transiently permeable to naked DNA.

Natural genetic transformation is the process by which a given bacterial strain can be transformed, i.e. modified to integrate a polynucleotide in its genome, through natural competence.

Streptococcal natural competence has been most extensively studied in *Streptococcus pneumoniae*, and appears to be a common feature to streptococci species. Competence is generally tightly regulated and involves two sets of genes: the early and the late competence genes (4). In *S. pneumoniae*, natural competence is a transient event that relies on the accumulation of a pheromone (CSP) in the growth medium. The early competence genes encode a two-component system (TCS: ComD and ComE), its cognate induction factor (CSP: ComC), and the components of an ABC transporter dedicated to CSP export and maturation (ComA and ComB). Upon CSP induction, TCS activates transcription of the competence sigma factor ComX ($\sigma X$). This alternative sigma factor is the central regulator of natural competence since it positively regulates all essential late genes necessary for DNA uptake, protection and integration into the chromosome (4). See FIG. 1 for schematic representation.

A putative comX gene and other genes resembling all late competence genes essential for *S. pneumoniae* natural competence were found in the *S. thermophilus* genome (1). Moreover, putative "ComX-boxes" recognized by $\sigma^X$ were in silico-identified upstream of all operons containing essential late competence genes. This maintenance of all essential genes for natural competence in *S. thermophilus* suggested that they play a key physiological function (use of DNA as a nutrient, genome plasticity . . . ) in its ecological niche (1). In 2006, the group of Havarstein (5) has shown the functionality of natural competence in *S. thermophilus* LMG18311 through the use of genetic engineering methodologies. This was achieved by using a plasmid-based system containing comX under the control of a regulated peptide-induced promoter (blp system, (6)). Remarkably, high transformation frequency ($10^{-3}$ to $10^{-2}$) was achieved with an efficacy similar to *S. pneumoniae* with either total genomic DNA or linear dsDNA (5). It is noticeable that in this case, induction of late competence genes was artificially made possible through the genetically engineered induction of ComX. However and surprisingly, none of the early competence genes usually found in *S. pneumoniae* genomes and that play a crucial role in the induction of natural competence are present in *S. thermophilus* genomes. Recently, it was demonstrated that competence in *S. thermophilus* LMD-9 can be induced during growth in a chemically defined medium. In strain LMD-9, the transporter Ami was shown to be specifically required for the transcriptional induction of comX in those conditions (7). The Ami system actively imports oligopeptides present in the extracellular medium and is known to have both nutritive and signaling functions in Gram-positive bacteria (7, 8, 9). Since this chemically defined medium is a peptide-free medium, Gardan et al. (7) hypothesized that, in those growth conditions, the bacterium synthesizes and secretes a specific competence-stimulating peptide, which is then sensed and re-imported by the Ami system. Once internalized, this pheromone would then interact with a specific cytoplasmic regulator, leading to the transcriptional induction of comX (for a model, see FIG. 2). The pheromone and the transcriptional regulator responsible for comX expression and natural transformation in the chemically defined medium conditions are still unknown.

Although natural transformation in chemically defined medium was very efficient in strain LMD-9 ($10^{-4}$ to $10^{-3}$), the transformation rate of strain LMG18311 was remarkably lower ($10^{-7}$ to $10^{-6}$). In addition, no transformant could be detected in the case of strain CNRZ1066 grown in chemically defined medium (transformation rate <$10^{-8}$) (7). To the inventors' knowledge, there is no successful report of a method to induce natural competence in strains of *S. thermophilus* without genetic engineering.

There is still a need in the art for a method for inducing natural competence in a *Streptococcus* bacterium, preferably in a *S. thermophilus* and/or a *S. salivarius* bacterium, and for transforming said bacterium, using a technology that is recognized world-wide as non-GMO.

DESCRIPTION OF THE INVENTION

The inventors have identified a novel Short Hydrophobic Peptide, Shp316, having the amino acid sequence as set forth in SEQ ID NO:1, that is involved in natural competence in *Streptococcus thermophilus* strains. Further, they have demonstrated that fragments of this peptide are capable of inducing natural competence in a bacterium belonging to the *Streptococcus* genus.

Shp316 has the following amino acid sequence:

MKTLKIFVLFSLLIAILPYFAGCL.    (SEQ ID NO: 1)

Consequently, the invention relates to a peptide having the amino acid sequence as set forth in SEQ ID NO:1 or having at least 75% identity with SEQ ID NO:1 or a fragment of said peptide, wherein said peptide or fragment thereof is capable of inducing or increasing competence in a *S. thermophilus* strain.

Typically, said peptide or fragment thereof is capable of inducing or increasing competence in the *S. thermophilus* strain LMD-9 in which the gene encoding SEQ ID NO:1 has been inactivated.

In the present application, the expression "the peptide of the invention" encompasses both the peptide having the amino acid sequence SEQ ID NO:1, the peptides with an amino acid sequence of a certain similarity with SEQ ID NO:1 (at least 75% identity) and fragments thereof (also named "mature" peptides). Examples of peptides according to the invention are disclosed in Annex III.

When referring to a peptide, the expression <<capable of inducing or increasing competence in the *S. thermophilus* strain LMD-9 in which the gene encoding SEQ ID NO:1 has been inactivated>> refers to any peptide which is capable of increasing the transformation rate by a factor of at least 10, preferably at least 50, at least 100, even more preferably at least 1000 in test A.

Test A, for testing the ability of a peptide to induce or increase competence, is performed as described in the Examples and as follows:

A mutant strain of LMD-9 in which the shp316 gene (which is the gene encoding the peptide Shp316) has been inactivated, such as strain LMD9-Δblp::P$_{comX}$-luxABΔ-shp316::P32-cat (see Example 2 for details on this strain) is pre-cultivated in M17-lactose medium. The cells of the pre-culture are harvested (5000 g, 9 minutes, 20° C.) and washed twice in Chemically Defined Medium (CDM, see Annex I) and then resuspended in CDM. The washed cells are diluted in fresh CDM medium to obtain an optical density of 0.05 at 600 nm, and then incubated at 37° C. After 1.5 h of incubation, the culture is separated in 2 aliquots of 10 mL and 0 or 1000 nM of peptide are added in the culture samples. Finally, each 10 mL-aliquot is divided in 2 samples of 5 mL each. One of the 2 samples receives 1 μg/mL pGIUD0855ery, a plasmid bearing an erythromycin resistance gene. The competence phenotype of the samples is studied by performing natural transformation experiments as described in example 1. The cultures are grown for 6 hours and serial dilutions are plated on the surface of M17-lactose agar medium containing or not 2.5 μg/mL of erythromycin. The transformation rate in the presence or absence of peptide is calculated for each sample; it is expressed as the ratio of erythromycin-resistant cells among the total bacterial population.

The peptide is deemed to have induced or increased competence in the LMD-9 strain in which the shp316 gene has been inactivated if the ratio of the transformation rate in the presence of the peptide to the transformation rate in the absence of peptide is at least 10, preferably at least 50, more preferably at least 100, even more preferably at least 1000.

The peptide of the invention may have at least 75% identity with SEQ ID NO:1, preferably at least 79% identity with SEQ ID NO:1, more preferably at least 83% identity with SEQ ID NO:1, even more preferably at least 87% identity with SEQ ID NO:1, even more preferably at least 91% identity with SEQ ID NO:1, even more preferably at least 95% identity with SEQ ID NO:1.

According to a preferred embodiment of the invention, the C-terminal end of a peptide of the invention has the following amino acid sequence: AGCL (SEQ ID NO: 89) or TGCL (SEQ ID NO: 131).

According to a preferred embodiment of the invention, the C-terminal end of a peptide of the invention has the following amino acid sequence: PYFAGCL (SEQ ID NO: 86), LPYFAGCL (SEQ ID NO: 85), ILPYFAGCL (SEQ ID NO: 84), AILPYFAGCL (SEQ ID NO: 83) or PYFTGCL (SEQ ID NO: 128).

In a particular embodiment the peptide has the following amino acid sequence:

MKTLKIFVLFSLLIPILPYFAGCL    (SEQ ID NO: 2)

This sequence has more than 95% identity with SEQ ID NO:1. This peptide was deduced from the genome of the *S. thermophilus* strain CNCM I-2423, a strain deposited by Rhodia Food SAS (B.P. 10, Z.A. de Buxières, 86220 Dangé-Saint-Romain) at the CNCM (Collection Nationale de Cultures de Microorganismes, 28 rue du Docteur Roux, 75724 Paris CEDEX 15, France) on the 5th of Apr. 2000 under number CNCM I-2423.

In another particular embodiment the peptide has the following amino acid sequence:

MKKLKLFTLFSLLITILPYFTGCL    (SEQ ID NO: 3)

This sequence has more than 79% identity with SEQ ID NO:1 and more than 83% of similarity with SEQ ID NO:1. This peptide was deduced from the genome of the *S. salivarius* strain SK126 (accession number NZ_A-CLO01000018), strain known in the prior art. So in a particular embodiment the peptide of the invention may have at least 79% similarity with SEQ ID NO:1, preferably at least 83% similarity with SEQ ID NO:1, more preferably at least 87% similarity with SEQ ID NO:1, even more preferably at least 91% similarity with SEQ ID NO:1, even more preferably at least 95% similarity with SEQ ID NO:1.

Similarity between two amino acid sequences is determined by using a similarity score matrix based on chemical similarity or evolutionary distance between amino acids. An example of such a matrix commonly used is the BLOSUM62 matrix (12), the default matrix for the BLAST suite of programs.

In a particular embodiment the peptide of the invention may have:
at least 75% identity with SEQ ID NO:1, preferably at least 79% identity with SEQ ID NO:1, more preferably at least 83% identity with SEQ ID NO:1, even more preferably at least 87% identity with SEQ ID NO:1, even more preferably at least 91% identity with SEQ ID NO:1, even more preferably at least 95% identity with SEQ ID NO:1;

at least 84% identity over positions 6-24 of SEQ ID NO:1, more preferably at least 89% identity over positions 6-24 of SEQ ID NO:1 (corresponding to SEQ ID NO: 4), even more preferably at least 94% identity over positions 6-24 of SEQ ID NO:1 (corresponding to SEQ ID NO: 4).

Without wishing to be bound by theory, it is thought that Shp316 is the precursor of the competence-inducing peptide; Shp316 is matured and secreted in the extracellular medium in the form of a fragment (named "mature" Shp316) and at a critical concentration, said "mature" Shp316 induces competence through the activation of comX expression. The involvement of the oligopeptide transporter Ami in the signaling cascade (7) and of the Rgg regulator STER_0316 (see example 1) further suggests that "mature" Shp316 is re-imported into the cell to interact with STER_0316. This interaction would then activate STER_0316, which in turn, will directly or not, induce comX transcription (For a model, see FIG. 5).

Typically, the peptide of the invention can contain at least 7 amino acids, preferably at least 6 amino acids, even more preferably at least 5 amino acids, even more preferably at least 4 amino acids.

Typically, the peptide of the invention contains at most 24 amino acids, at most 23 amino acids, at most 22 amino acids, at most 21 amino acids, at most 20 amino acids, preferably at most 19, at most 18, at most 17, at most 16, at most 15, at most 14, at most 13, at most 12, at most 11, at most 10, at most 9, even more preferably at most 8, at most 7, at most 6, at most 5 or at most 4 amino acids.

Shp316 displays a positively-charged N-terminal end, a hydrophobic core and a short C-terminal sequence (CL). The sequence corresponding to the amino acids in position 6-24 is the sequence:

```
IFVLFSLLIAILPYFAGCL.        (SEQ ID NO: 4)
```

In one embodiment, the peptide of the invention has the amino acid sequence as set forth in SEQ ID NO: 4.

In another embodiment, the peptide of the invention comprises the amino acid sequence AGCL (SEQ ID NO: 89) or TGCL (SEQ ID NO: 131).

In another embodiment, the peptide of the invention comprises the amino acid sequence PYFAGCL (SEQ ID NO: 86), LPYFAGCL (SEQ ID NO: 85), ILPYFAGCL (SEQ ID NO: 84), AILPYFAGCL (SEQ ID NO: 83) or PYFTGCL (SEQ ID NO: 128).

In one embodiment, the peptide of the invention contains at least 7, preferably at least 6, even more preferably at least 5, even more preferably at least 4 consecutive amino acids selected from the amino acid sequence as set forth in SEQ ID NO: 4.

In a particular embodiment the peptide of the invention has the amino acid sequence PYFAGCL (SEQ ID NO: 86). It corresponds to the positions 18-24 of SEQ ID NO:1. This peptide was deduced from the genome of the *S. thermophilus* strain LMD-9 or strain CNCM I-2423.

In another particular embodiment the peptide of the invention has the amino acid sequence PYFTGCL (SEQ ID NO: 128). It corresponds to the positions 18-24 of SEQ ID NO:3. This peptide was deduced from the genome of the *S. salivarius* strain SK126 (accession number NZ_ACL001000018), strain known in the prior art.

In one embodiment, the peptide of the invention has an amino acid sequence selected from the group consisting of the sequences disclosed in Annex III.

In one aspect, the invention also relates to an isolated nucleic acid encoding a peptide as described above.

In a preferred embodiment, the isolated nucleic acid comprises the sequence as set forth in SEQ ID NO:6 or a sequence having at least 80% identity with SEQ ID NO:6.

SEQ ID NO:6 corresponds to shp316 (the gene encoding Shp316) and corresponds to the following sequence:

```
TTGAAAACCCTGAAAATATTTGTACTATTTTCACTACTTATTGCTATCTT

GCCTTATTTTGCAGGATGTCTTTAA
```

The isolated nucleic acid may have at least 80% identity with SEQ ID NO:6, preferably at least 85% identity with SEQ ID NO:6, more preferably at least 90% identity with SEQ ID NO:6, more preferably at least 95% identity with SEQ ID NO:6, even more preferably at least 98% identity with SEQ ID NO:6.

In a particular embodiment the isolated nucleic acid has the following sequence:

```
                                     (SEQ ID NO: 7)
TTGAAAACCCTGAAAATATTTGTACTATTTTCACTACTTATTCCTATCTT

GCCTTATTTTGCAGGATGTCTTTAA
```

This sequence has more than 98% identity with SEQ ID NO:6. It was detected in the genome of the *S. thermophilus* strain CNCM I-2423.

In a particular embodiment the isolated nucleic acid has the following sequence:

```
                                     (SEQ ID NO: 8)
TTGAAAAAACTAAAATTATTTACACTATTCTCACTACTTATCACTATCTT

GCCCTATTTTACAGGTTGTCTTTAA
```

This sequence has more than 84% identity with SEQ ID NO:6. It was detected in the genome of the *S. salivarius* strain SK126 (accession number NZ_ACLO01000018).

The invention also relates to a vector comprising an isolated nucleic acid as described above. Typically, said vector can be a plasmid, i.e. a circular double-stranded DNA molecule which is auto-replicative (i.e. it contains an origin of replication) or an integrative vector.

The peptides, nucleic acids and vectors described above can be used to induce or increase competence in a bacterium belonging to the *Streptococcus* genus, in particular a bacterium belonging to the *S. thermophilus* species or *S. salivarius* species.

Consequently, the peptides, nucleic acids and vectors of the invention are useful for transforming a bacterium belonging to the *Streptococcus* genus, in particular a bacterium belonging to the *S. thermophilus* species or *S. salivarius* species, by natural genetic transformation.

Therefore, the invention also relates to a method for inducing competence in a bacterium belonging to the *Streptococcus* genus comprising the step of transforming said bacterium with an expression vector as described above.

The invention also relates to a method (method B) for inducing and/or increasing competence in a bacterium belonging to the *Streptococcus* genus wherein said bacterium is incubated in a medium comprising a peptide according to the invention and/or a bacterium producing a peptide according to the invention.

The invention also concerns the competent bacteria and the bacteria with improved competence obtainable by this method B.

Particularly it concerns a kit-of-parts comprising:
a bacterium belonging to the *Streptococcus* genus in a first part; and
in a second part, a peptide according to the present invention and/or a bacterium producing a peptide according to the invention.

The invention also relates to a method (method C) for transforming a bacterium belonging to the *Streptococcus* genus by natural genetic transformation with a polynucleotide, comprising the steps of:
a) adding a peptide according to the invention and/or a bacterium producing a peptide according to the invention to the medium of said bacterium belonging to the *Streptococcus* genus; and
b) adding said polynucleotide.

Steps a) and b) can be carried out sequentially or simultaneously.

According to this method, the bacterium is incubated in a growth medium which comprises:
a) a peptide according to the invention.

The peptide can be added in several ways.

In a preferred embodiment, said peptide is added directly into the medium.

Typically, said peptide can be a synthetic peptide or a recombinant peptide. Methods for obtaining peptides are standard methods, well known to the skilled person in the art.

Typically, said peptide can be used at a concentration comprised between 100 nM and 10 µM, preferably between 500 nM and 2500 nM, even more preferably between 200 nM and 2000 nM, even more preferably at about 1000 nM.

In another embodiment, the peptide is secreted by a bacterium, which is added as a co-culture to the bacterium belonging to the *Streptococcus* genus.
b) the polynucleotide with which the bacterium belonging to the *Streptococcus* genus is to be transformed.

Typically the polynucleotide, when incorporated into the bacterium, confers to the bacterium an interesting phenotype, e.g. phage resistance, proteolytic activity, exopolysaccharide biosynthesis, natural competence. In one embodiment, the polynucleotide is a nucleic acid containing the gene shp316, as described above.

The polynucleotide may for example encode a protein such as a protease, a peptidase, a glycosyltranferase or a bacteriocin . . . .

Typically the polynucleotide may be a part of a gene sequence, a gene sequence, or a plurality of gene sequences. The polynucleotide may be linear or circular. Typically the polynucleotide may be a plasmid which may be auto-replicative in the transformed bacterium or not. Typically the polynucleotide may be designed to facilitate its incorporation within the genome of the bacterium by homologous recombination. The polynucleotide may be a single stranded linear DNA.

Typically the polynucleotide size is comprised between 10 bp and 100 kbp, preferably between 100 bp and 10 kbp, or between 100 bp and 50 kbp, more preferably between 500 bp to 30 kbp, even more preferably between 1 kbp to 20 kbp, more preferably between 500 bp to 25 kbp, even more preferably between 1 kbp to 16 kbp.

Typically the concentration of polynucleotide in the growth medium is comprised between 0.1 µg/L and 2 g/L, preferably between 0.5 µg/L and 1.5 g/L, more preferably between 1 µg/L and 1 g/l.

The invention also relates to a transformed bacterium obtainable by the method C described above.

The peptides, nucleic acids, vectors, methods and bacteria described above can be used to improve *Streptococcus* bacterial strains, and in particular strains of *S. thermophilus* or *S. salivarius*, for the fermented food and feed industry (or other industry using *S. thermophilus* or *S. salivarius* strains) by transferring interesting traits (proteolytic activity, amino acid biosynthesis, bacteriocin production, exopolysaccharide production, production of flavouring metabolite, phage resistance, natural competence . . . ) from the DNA of one strain to another strain, allowing the generation of unique combinations in the same genetic background. It falls within the ability of the skilled person in the art to select the appropriate polynucleotide to be used for this transformation, depending on the desired trait.

The bacteria belonging to the *Streptococcus* genus obtained according to the methods described above (methods B and C) may be used in the food industry, in particular for the manufacture of a dairy product. Typically, the bacterium is classified as Generally Recognized As Safe (GRAS).

Consequently, the invention also relates to a method for obtaining a food product or a feed product, comprising the step of using a bacterium obtained according to the methods described above (methods B and C).

The invention also relates to a food product or a feed product obtainable by said method.

The invention also relates to a food product or a feed product containing a bacterium obtained according to the methods described above (methods B and C).

In a preferred embodiment, for the methods described above (method B and method C) said bacterium belonging to the *Streptococcus* genus expresses STER_0316, the gene which encodes the transcriptional regulator STER_0316.

Indeed, the inventors have also discovered a method for blocking the natural competence in a bacterium belonging to the *Streptococcus* genus, in particular a bacterium belonging to the *Streptococcus thermophilus* species. Indeed, they have found that both Shp316 (or any "mature" Shp316) and its cognate regulator STER_0316 are necessary for natural competence.

Accordingly, another aspect of the invention concerns the transcription regulator (Rgg) STER_0316 (SEQ ID NO:9).

The invention thus relates to a polypeptide having the amino acid sequence as set forth in SEQ ID NO:9 or a variant thereof having at least 85% identity with SEQ ID NO:9, preferably at least 90% identity with SEQ ID NO:9, more preferably at least 95% identity with SEQ ID NO:9, even more preferably at least 98% identity with SEQ ID NO:9.

In a particular embodiment the polypeptide has the sequence SEQ ID NO:10.

This sequence has more than 98% identity with SEQ ID NO:9. It was deduced from the genome of the *S. thermophilus* strain CNCM I-2423.

In a particular embodiment the polypeptide has the sequence SEQ ID NO:11.

This sequence has more than 93% identity with SEQ ID NO:9. It was deduced from the genome of the *S. salivarius* strain SK126.

The invention also relates to an isolated nucleic acid STER_0316 (which encodes the transcription regulator STER_0316), comprising SEQ ID NO:12 or a variant thereof having at least 80% identity with SEQ ID NO:12, preferably at least 85% identity with SEQ ID NO:12, preferably at least 90% identity with SEQ ID NO:12, more preferably at least 95% identity with SEQ ID NO:12, even more preferably at least 98% identity with SEQ ID NO:12.

In a particular embodiment the isolated nucleic acid has the sequence SEQ ID NO:13.

This sequence has more than 99% identity with SEQ ID NO:12. It was detected in the genome of the S. thermophilus strain CNCM I-2423.

In a particular embodiment the isolated nucleic acid has the sequence SEQ ID NO:14.

This sequence has more than 91% identity with SEQ ID NO:12. It was detected in the genome of the S. salivarius strain SK126.

The invention also relates to a method for blocking natural competence in a bacterium belonging to the Streptococcus genus, in particular a bacterium belonging to the S. thermophilus species or S. salivarius species, comprising the step of inactivating the STER_0316 gene and/or the shp316 gene.

The invention also relates to a method for increasing natural competence in a bacterium belonging to the Streptococcus genus, in particular a bacterium belonging to the S. thermophilus species or S. salivarius species, comprising the step of overexpressing the STER_0316 gene and/or the shp316 gene.

The terms "STER_0316 gene" and "shp316 gene" include the STER_0316 and shp316 genes described above for the S. thermophilus strain LMD-9 (respectively SEQ ID No 12 and SEQ ID No 6) and their respective homologues in S. thermophilus strain CNCM I-2423 and S. salivarius SK126 and other S. thermophilus species or S. salivarius species.

In a particular embodiment the invention concerns mutants of a bacterium that are unable to express STER_0316 and/or shp316 or that do not have these genes in their genome, wherein the STER_0316 and/or shp316 gene(s) is (are) introduced.

FIGURES

FIG. 1: Schematic representation of the induction of competence for DNA transformation in S. pneumoniae and S. mutans
  (1) During growth of S. pneumoniae and S. mutans, the transcription of the precursor of the competence pheromone gene comC is triggered.
  (2 and 3) The gene comC is translated and secreted in the extracellular medium through the ComAB ABC-transporter. During its secretion, the precursor peptide ComC is matured into CSP peptide which accumulates in the extracellular medium.
  (4) At a critical concentration, the mature CSP is recognized by the histidine kinase ComD, which catalyses its auto-phosphorylation.
  (5) The phosphate group is transferred to the cytoplasmic regulator ComE, which activates the latter.
  (6) The phosphorylated ComE regulator activates the transcription of comX and the early essential competence genes comABCDE.
  (7) comX associates with the RNA polymerase core and activates the transcription of the genes essential for DNA transformation.

Figure 2:
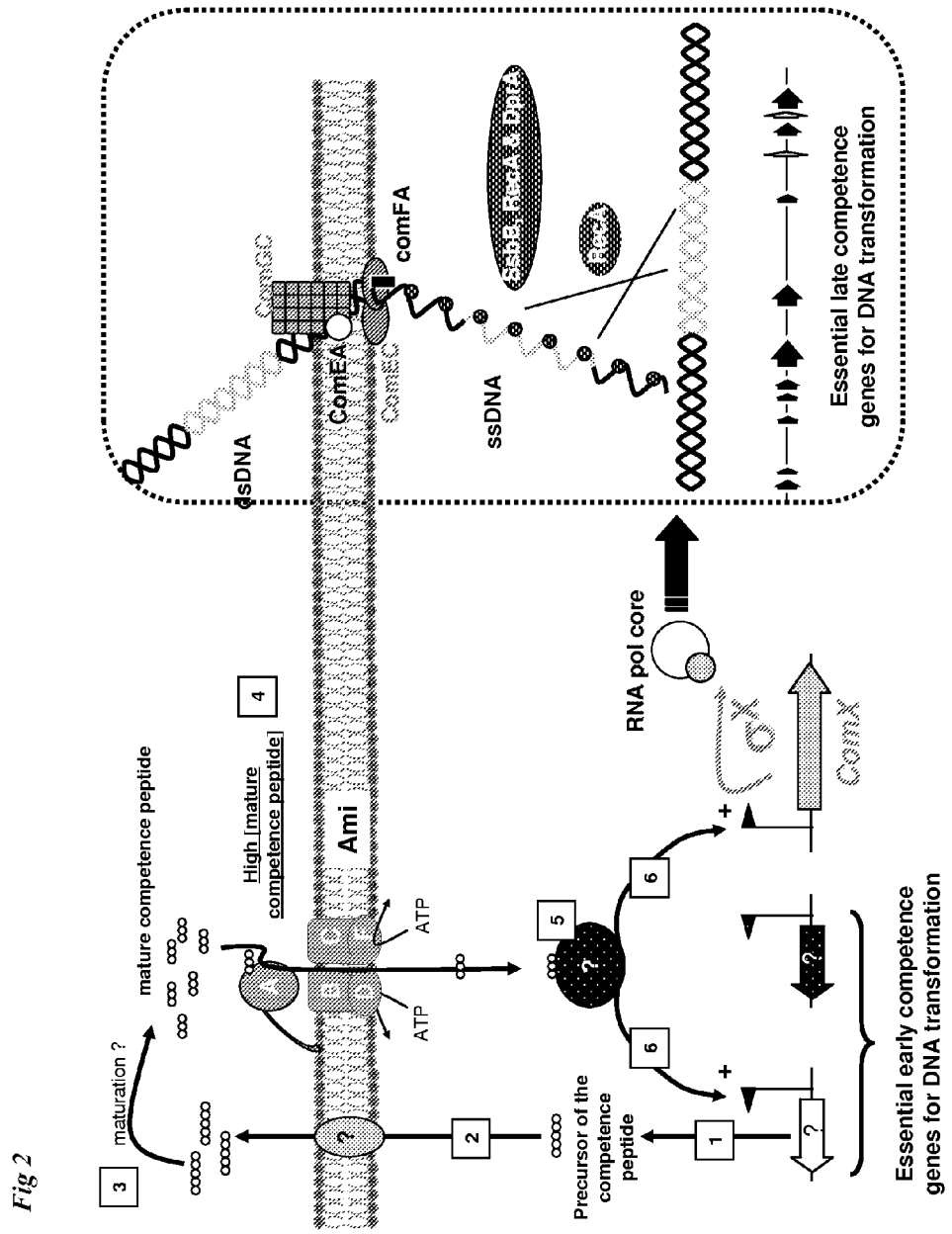

FIG. 2: Schematic representation of the model for the induction of comX expression in strain LMD-9 in Chemically defined medium (CDM) (adapted from Gardan et al., 2009; J. Bacteriol.).
  (1) In CDM growth conditions, the expression of the specific gene encoding the precursor of the competence pheromone is probably induced.
  (2) The corresponding pheromone is translated and could then be secreted in the extracellular medium where it could eventually be matured (3).
  (4) At a critical concentration, the competence pheromone could be specifically recognized and internalized by the Ami transporter.
  (5) Once in the cytoplasm, the pheromone could interact with a specific transcriptional regulator leading to its activation and the subsequent transcriptional induction of comX (6).

Figure 3:
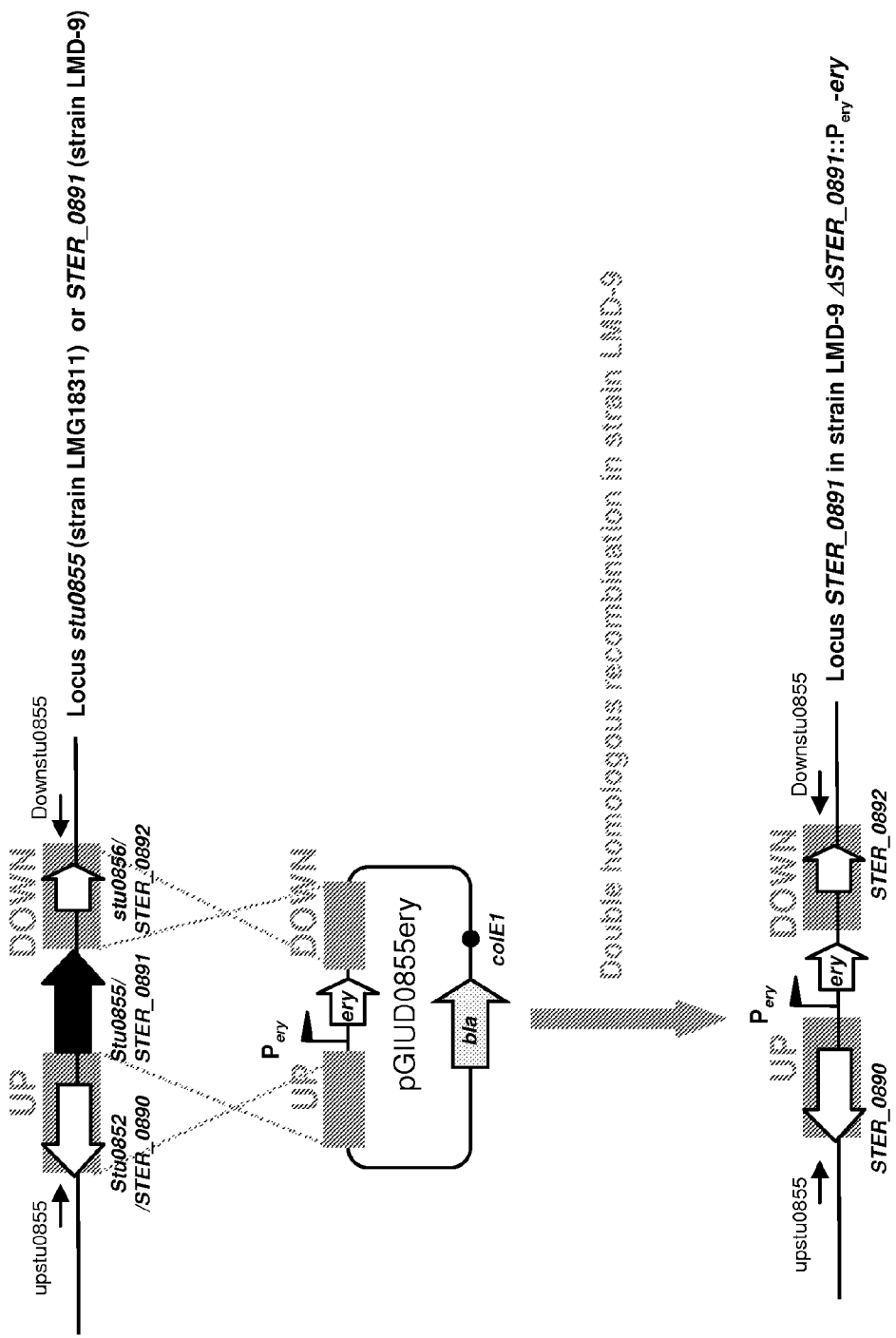

FIG. 3: Schematic representation of the strategy used to test the natural transformation rate of S. thermophilus LMD-9, LMG18311 and CNRZ1066. The exogenous DNA used in the transformation experiment is the suicide plasmid pGIUD0855ery. This plasmid is a pUC18 derivative which contains two fragments of approximately 1 kb, corresponding to the upstream (UP) and downstream (DOWN) regions of stu0855 from strain LMG18311. It also contains an expression cassette consisting of a fusion between the promoter $P_{ery}$ and the erythromycin resistance gene ery. The UP and DOWN region of stu0855 were cloned respectively ustream and downstream of the $P_{ery}$-ery cassette of pUC18 to obtain plasmid pGIUD0855ery. During the natural transformation process, the $P_{ery}$-ery cassette of PGIUD0855ery will integrate at the STER_0891 locus (stu0855 or str0855 locus, depending on the recipient strain) by double homologous recombination (represented by dotted lines), and replace STER_0891 open reading frame (or stu0855, or str0855 open reading frame) in the chromosome. The primers pair upstu0855/Downstu0855 used to check the integration of $P_{ery}$-ery at the expected locus are represented by arrows.

Figure 4:
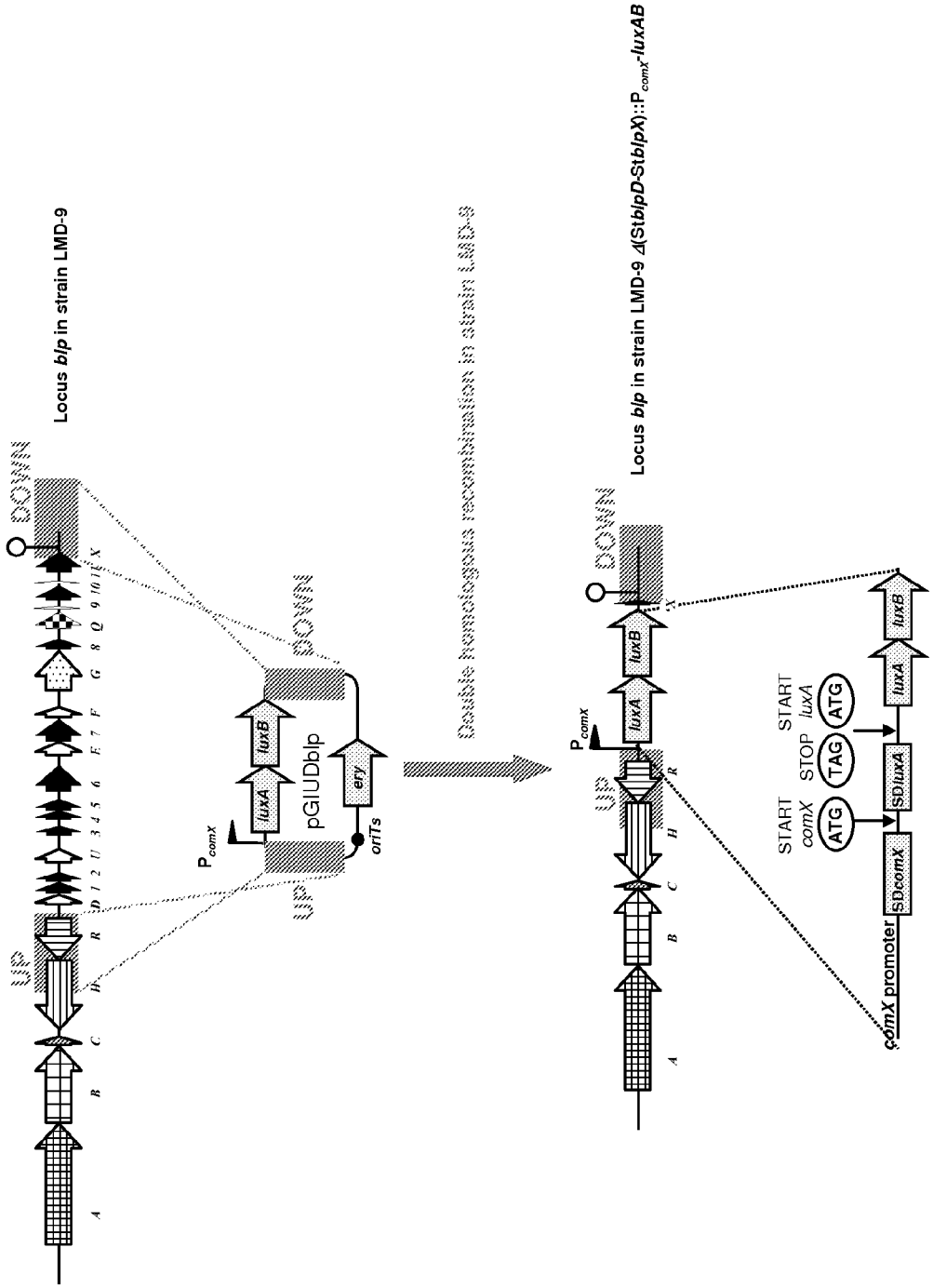

FIG. 4: Schematic representation of the strategy used to construct S. thermophilus LMD-9 Δ(StblpD-StblpX)::$P_{comX}$-luxAB. The vector pGIUDblp is a pGhost9 derivative (Maguin, E., P. Duwat, T. Hege, D. Ehrlich, and A. Gruss. 1992. New thermosensitive plasmid for gram-positive bacteria. J. Bacteriol. 174:5633-5638). This vector was obtained by successively cloning two fragments of approximately 1 kb, corresponding to the upstream (UP) and downstream (DOWN) regions of the Blp bacteriocin genes from strain LMD-9, respectively. The pGIUDblp vector also contains an expression cassette consisting of a fusion between the promoter $P_{comX}$ from S. thermophilus LMD-9 and the luxAB genes from Photorabdus luminescens (the fusion is described at the bottom of the figure). This cassette was cloned between the UP and DOWN region of pGIUDblp. The replacement of blp genes by the $P_{comX}$-luxAB cassette was performed by a two-step homologous recombination process (represented by dotted lines), as previously described (Maguin, E., H. Prevost, S. D. Ehrlich, and A. Gruss. 1996. Efficient insertional mutagenesis in lactococci and other gram-positive bacteria. J. Bacteriol. 178:931-935).

Figure 5:
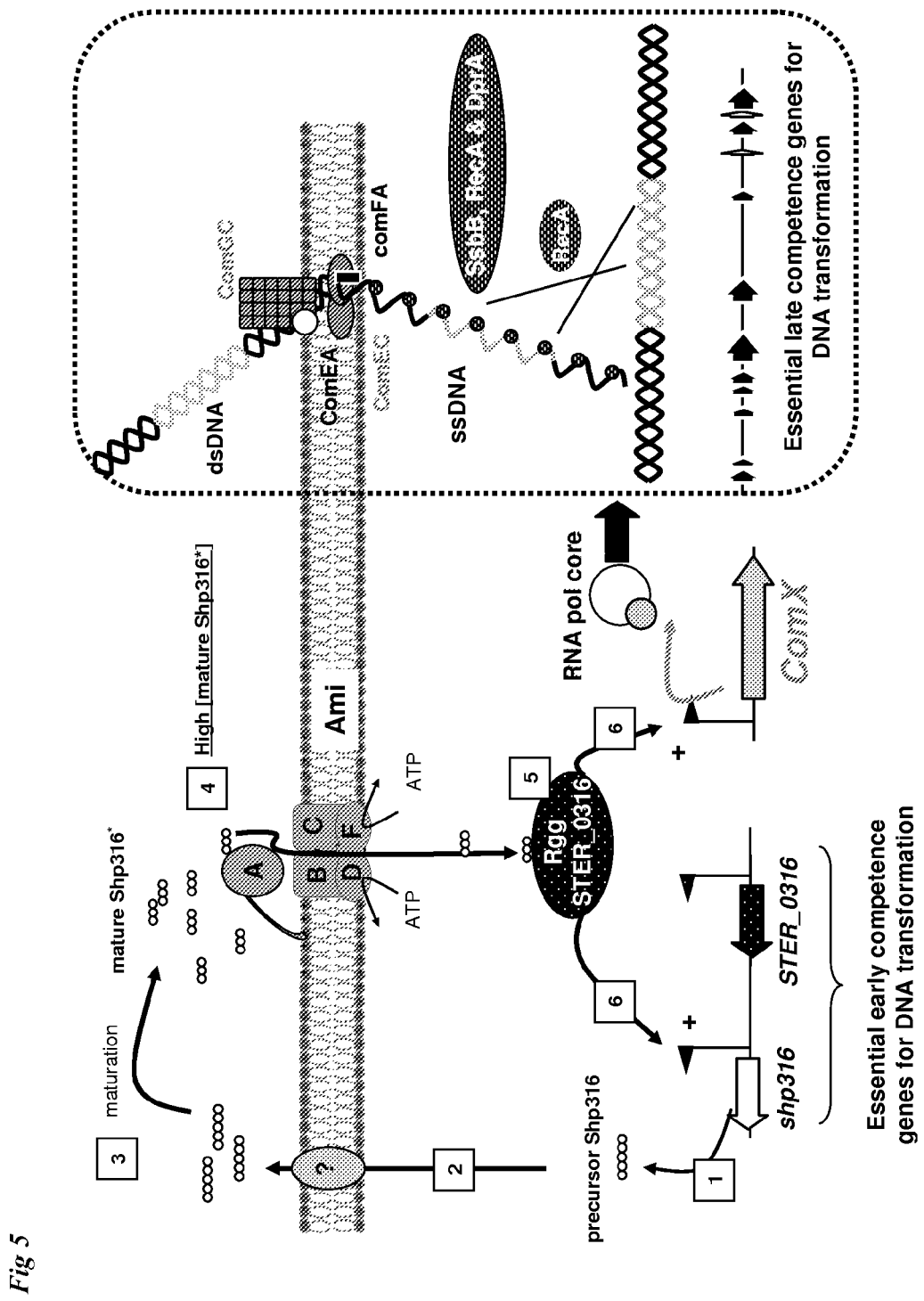

FIG. 5: Schematic representation of the model for the induction of comX expression in strain LMD-9 in Chemically defined medium (CDM) (deduced from the examples described above).
  (1) In CDM growth conditions, the transcription of the precursor of the competence pheromone gene shp316 is triggered.
  (2 and 3) The gene shp316 is translated and secreted in the extracellular medium through a yet unidentified secretion system. The precursor peptide Shp316 is matured and accumulates in the extracellular medium.
  (4) At a critical concentration, the mature Shp316* is recognized and internalized by the oligopeptide Ami transporter.
  (5) Mature Shp316* interacts and activates the transcriptional regulator STER_0316.
  (6) The regulator STER_0316 activates the transcription of comX and shp316.

Figure 6:
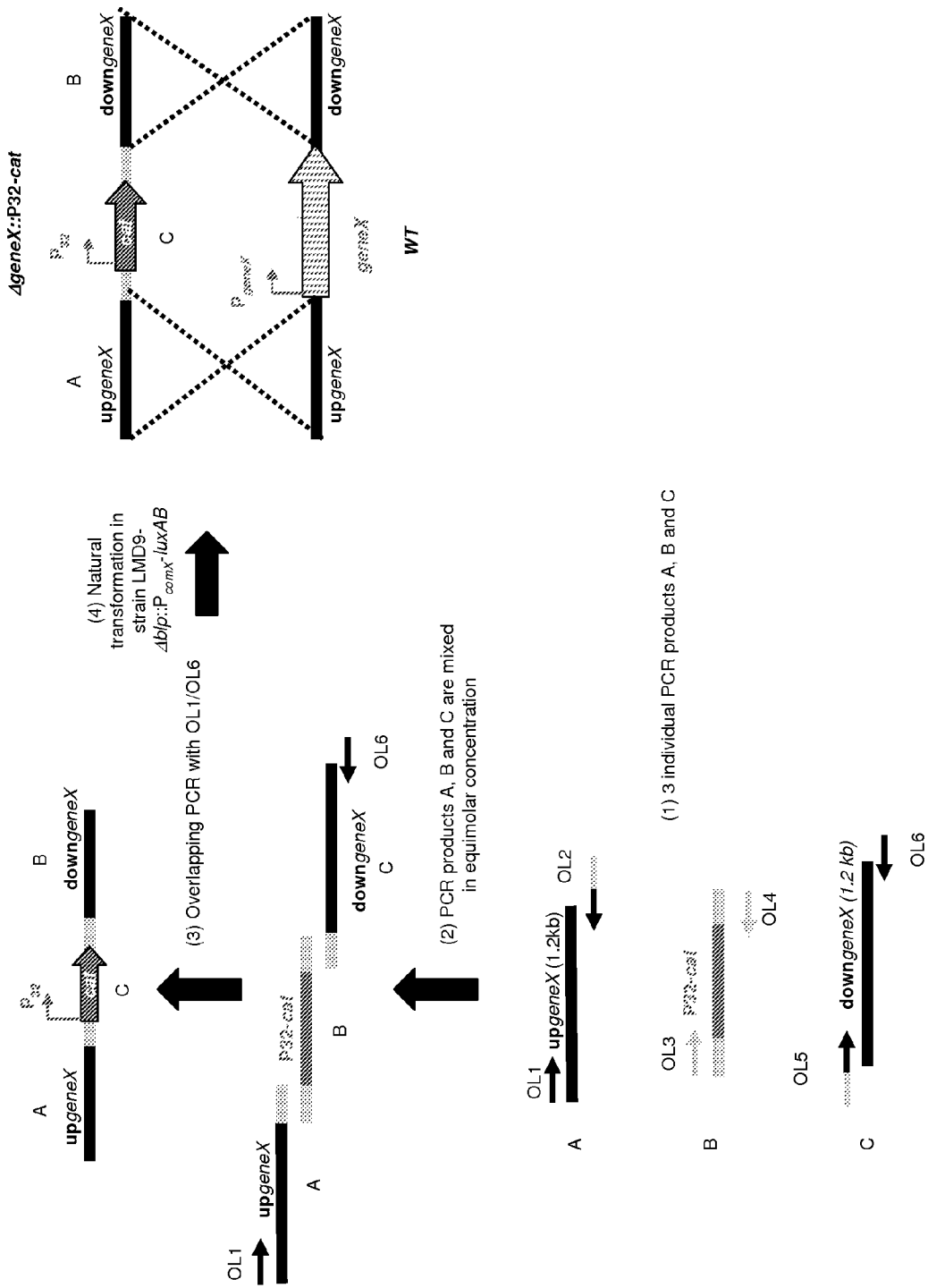

FIG. 6: Schematic representation of the strategy used to perform targeted mutagenesis in *S. thermophilus*.
(1) Three individual PCR reactions are preformed to amplify fragments A, B and C. Fragment A corresponds to the upstream region of the gene of interest i.e. the gene that has to be deleted. Fragment A is amplified with the primer pair OL1/OL2. Fragment B corresponds to a chloramphenicol expression cassette $P_{32}$-cat and is amplified with primer pair OL3/OL4. Fragment C corresponds to the downstream region of the gene of interest and is amplified with the primer pair OL5/OL6. The sequence of OL3 and OL4 are respectively complementary to the 5' end of OL2 and 5' end of OL5 (light grey line).
(2) The PCR products A, B and C are mixed in equimolar concentration
(3) An overlapping PCR is performed with the primer pair OL1/OL6 to join fragments A, B and C together.
(4) The overlapping PCR product is transferred through natural competence in strain LMD-9 Δ(StblpD-StblpX)::$P_{comX}$-luxAB grown in CDM. The P32-cat cassette replaces the gene of interest by double homologous recombination.

Figure 7:
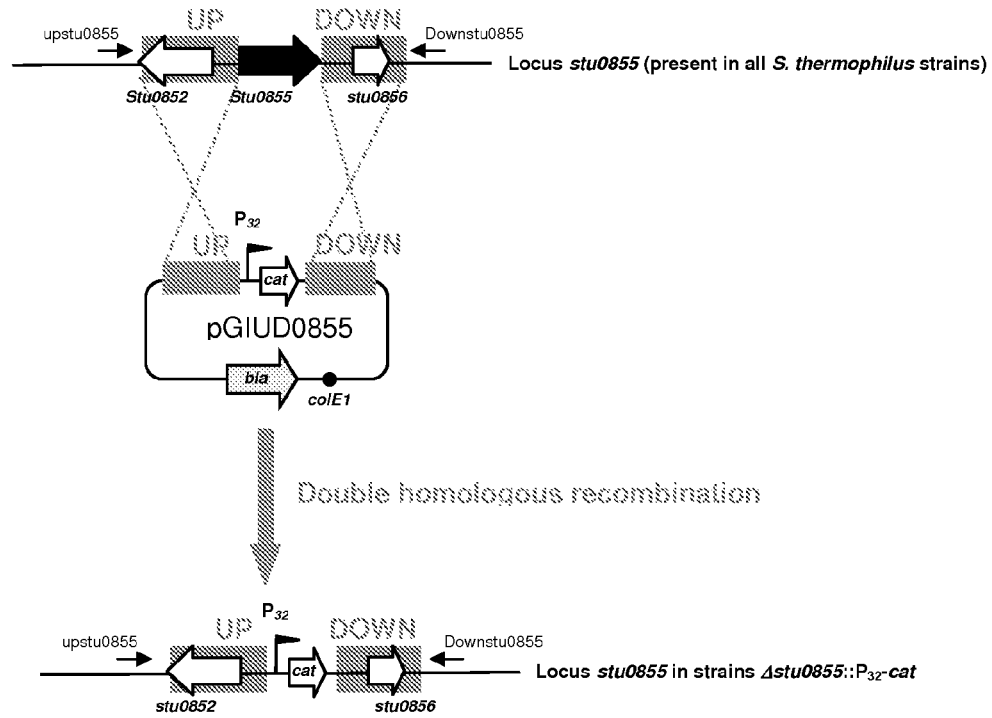

FIG. 7: Schematic representation of the strategy used to test the natural transformation rate of *S. thermophilus* strains. The exogenous DNA used in the transformation experiment is the suicide plasmid pGID0855cat. This plasmid is a pUC18 derivative which contains two fragments of approximately 1 kb, corresponding to the upstream (UP) and downstream (DOWN) regions of stu0855 from strain LMG18311. It also contains an expression cassette consisting of a fusion between the constitutive promoter $P_{32}$ from *Lactococcus lactis* and the chloramphenicol resistance gene cat. This cassette was cloned between the UP and DOWN region of pGID0855cat. During the natural transformation process, the P32-cat cassette of PGIUD0855cat will integrate at the stu0855 locus by double homologous recombination (represented by dotted lines), and replace stu0855 open reading frame in the chromosome. The primers pair upstu0855/Downstu0855 used to check the integration of $P_{32}$-cat at the expected locus are represented by arrows. The presence of the stu0855 locus in all *S. thermophilus* strains was PCR-checked prior to any experiment (data not shown).

Figure 8:
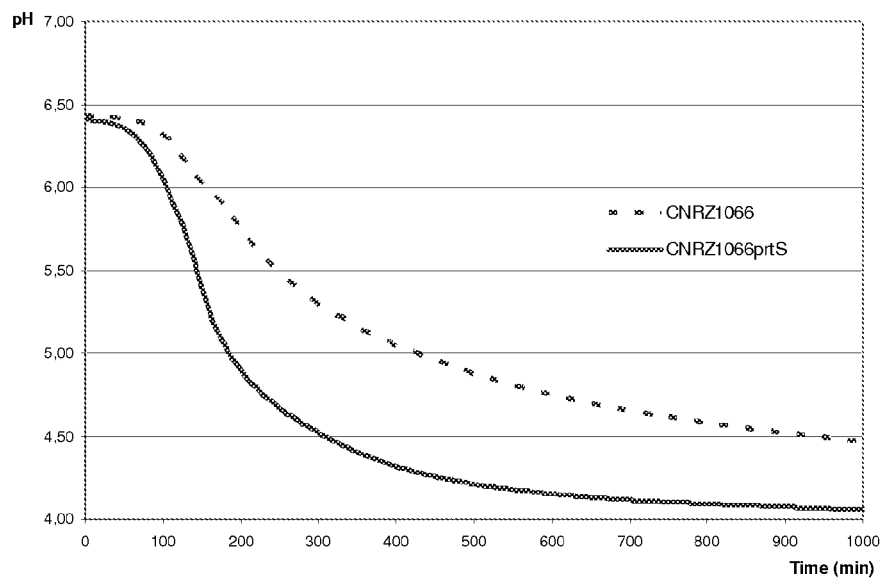

FIG. 8: Acidification kinetic of CNRZ1066 and CNRZ1066prtS cultivated in milk at 42° C.

FIG. 9: Schematic representation of the his locus in strain LMD-9 (A) and strain LMG18311 (B). Small black arrows represent the primers used in further construction and analyses.

Figure 10:
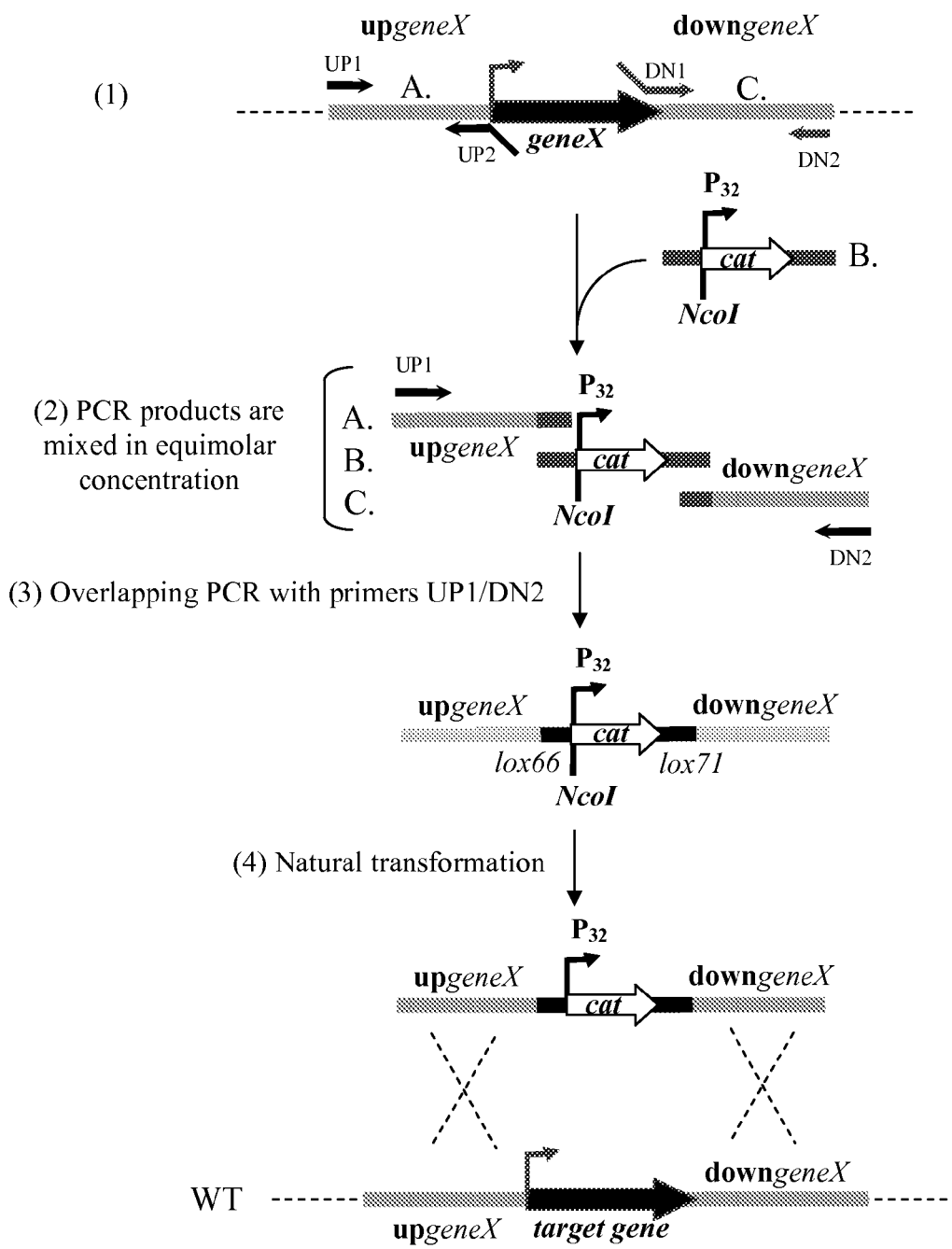

FIG. 10: Schematic representation of the strategy used to perform targeted mutagenesis in *S. thermophilus*.
(1) Three individual PCR reactions are preformed to amplify fragments A, B and C. Fragment A corresponds to the upstream region of the gene of interest i.e. the gene that has to be deleted. Fragment A is amplified with the primer pair UP1/UP2 (black arrows). Fragment B corresponds to a chloramphenicol expression cassette P32-cat and is amplified with primer pair Uplox66/DNlox71. Fragment C corresponds to the downstream region of the gene of interest and is amplified with the primer pair DN1/DN2. The sequence of Uplox66 and DNlox71 are respectively complementary to the 5' end of UP2 and 5' end of DN1.
(2) The PCR products A, B and C are mixed in equimolar concentration
(3) An overlapping PCR is performed with the primer pair UP1/DN2 to join fragments A, B and C together.
(4) The overlapping PCR product is transferred through natural competence in strain LMD-9 grown in CDM. The P32-cat cassette replaces the gene of interest by double homologous recombination.

Figure 11:
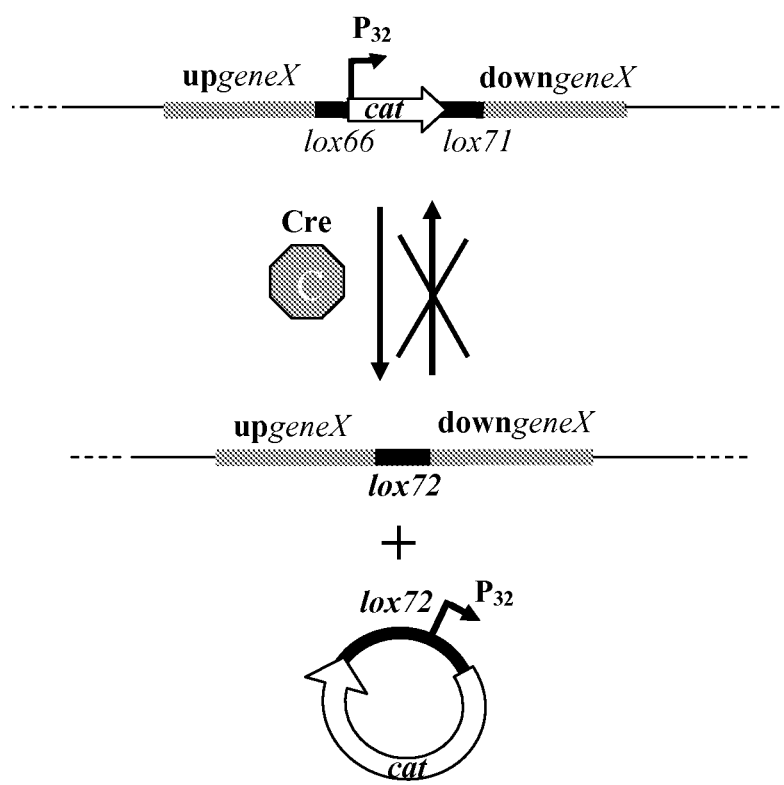

FIG. 11: Removal of the lox66-P32cat-lox71 cassette from the chromosome achieved by Cre-mediate excision.
The mutant lox66 and lox71 sites are, after Cre recombination, recombined into a double-mutant lox72 site which strongly reduced binding affinity for Cre.

Figure 12:
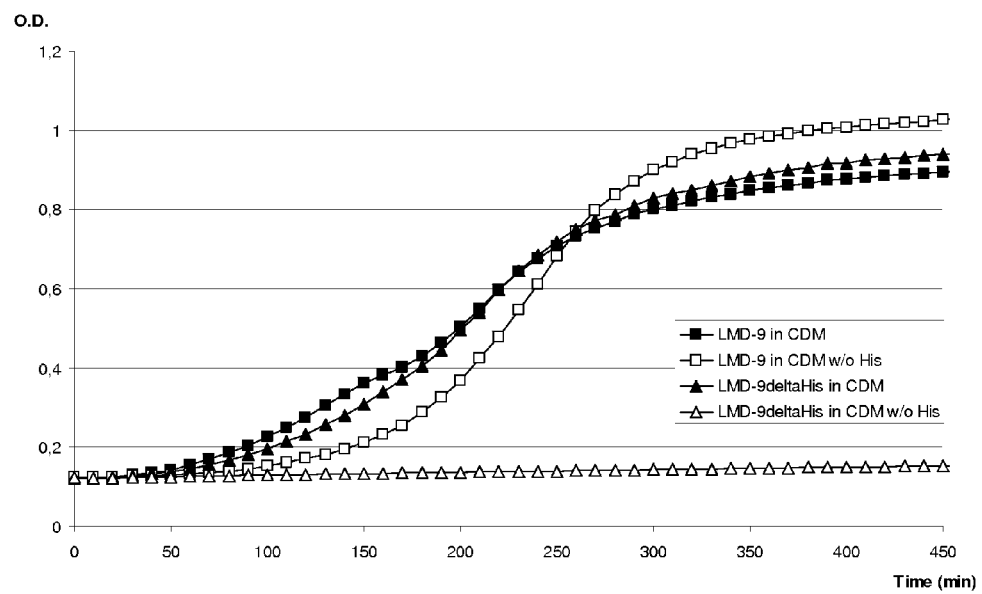

FIG. 12: Comparative growth of LMD-9 (squares) and of LMD-9deltaHis (triangles) in CDM (black symbols) and CDM deprived of histidine (white symbols).

Figure 13:
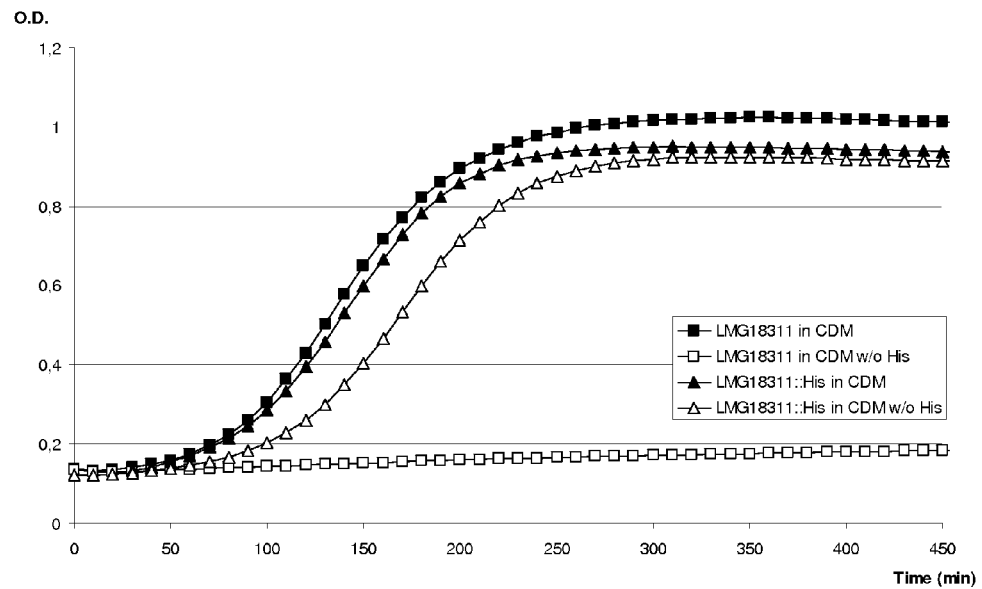

FIG. 13: Comparative growth of LMG18311 (squares) and LMG18311::His (triangles) in CDM (black symbols) and CDM deprived of histidine (white symbols).

Figure 14:
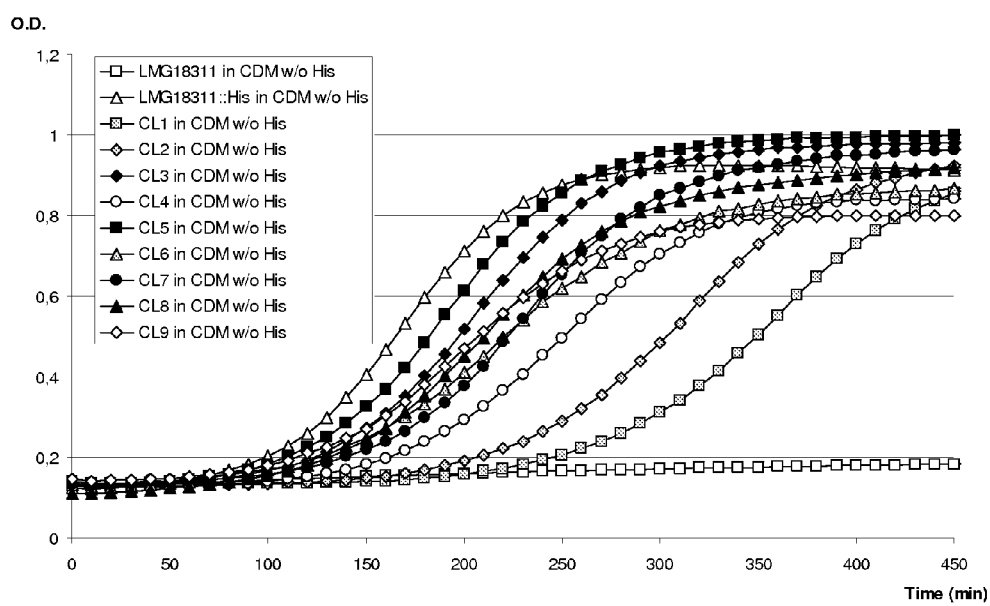

FIG. 14: Comparative growth in CDM deprived of histidine of LMG18311, LMG18311::His and of various his-positive isolates obtained by naturally induced transformation with LMD-9 DNA extracts.

EXAMPLES

The experiments described below provide evidence that natural competence in *Streptococcus thermophilus* and *S. salivarius* is strictly dependent on the secretion and sensing of a signaling peptide, derived from the peptide Shp316 encoded by shp316 gene.

Specifically, the examples below demonstrate that:
The gene STER_0316 (SEQ ID NO:12) encodes the transcriptional regulator (Rgg) (SEQ ID NO:9) responsible for comX induction.
The shp316 gene (SEQ ID NO:6) is the structural gene for the competence pheromone Shp316 (Short Hydrophobic Peptide 316) (SEQ ID NO:1).
The competence defect of a strain deleted for shp316 can be restored by a plasmid bearing shp316.
The competence defect of a strain deleted for shp316 can be restored by the addition of synthetic peptides derived from Shp316 in the medium.
The low transformation rates of strains *S. thermophilus* LMG18311 and CNRZ1066, and *S. salivarius* JIM8777 in chemically defined medium (CDM) can be improved by the addition in the medium of a synthetic peptide derived from Shp316.
A synthetic peptide derived from Shp316 is able to induce natural competence in most of *S. thermophilus* strains.
Natural competence can be used to beneficially modify functional traits of *S. thermophilus* strains such as nutritional requirements and acidification properties.

The experiments were conducted on *S. thermophilus* LMD-9, LMG18311 and CNRZ1066, which are typical safe *S. thermophilus* strains, and on *S. salivarius* JIM8777, which was isolated from the human oral cavity. Other strains were also tested in experiment 6.

1. The Deletion of STER_0316 Impairs comX Induction and Natural Transformation in CDM A *S. thermophilus* strain was constructed in order to have luminescence genes under the control of the promoter of comX gene. In such a construct, a luminescence increase will only be measured when the comX gene is expressed. The constructed strain was named LMD9-Δblp::$P_{comX}$-luxAB. The construct is presented in FIG. 4. In this construct, part of the blp operon (from blpD to blpX) was deleted (6) and replaced by a reporter cassette in which the luciferase genes luxAB of *Photorabdus luminescens* are fused to $P_{comX}$. This promoter was chosen because it was demonstrated that comX is strongly induced during development of natural competence in S. thermophilus LMD-9 growing in CDM (7).

The inventors performed the deletion of a Rgg-encoding gene, STER_0316, in strain LMD9-Δblp::$P_{comX}$-luxAB. The protocol used to perform targeted mutagenesis is described below (see FIG. 6). DNA fragments containing the desired insertion/deletion were made in vitro by overlapping PCR and transferred by competence in strain LMD9-Δblp::$P_{comX}$-luxAB in CDM growth conditions (7). The overlapping fragment consists of two 1.2 kb-recombining fragments flanking the target gene and separated by a P32-cat fragment (FIG. 6). The desired mutant was then selected on chloramphenicol-containing M17-lactose agar medium (5 μg/mL chloramphenicol) and its identity is checked by PCR with the primer pair Ch0316A/Ch0316B.

The following primers were used:

OL1:
(SEQ ID NO: 15)
5'-AAACAATGGTGGCCCAGGATCAATGATTGGG-3'

OL2:
(SEQ ID NO: 16)
5'-CCTTATGGGATTTATCTTCCTTAGATTCTTAGTCCAATGCT-3'

OL3:
(SEQ ID NO: 17)
5'-TAAGGAAGATAAATCCCATAAGG-3'

OL4:
(SEQ ID NO: 18)
5'-TTCACGTTACTAAAGGGAATGTA-3'

OL5:
(SEQ ID NO: 19)
5'-TACATTCCCTTTAGTAACGTGAAGTTTTGGAAGACTCGG-3'

OL6:
(SEQ ID NO: 20)
5'-CAATAATAGCAGTATTGACCTGACTATTTGCCTCC-3'

Ch0316A:
(SEQ ID NO: 21)
5'-TAAGAGTGCTATTGGTGTTCTCTTGC-3'

Ch0316B:
(SEQ ID NO: 22)
5'-TCATGGAATTTCACCTCAATTTCTTGC-3'

The impact of the deletion of the Rgg-encoding gene STER_0316 on competence was evaluated by monitoring the luminescence driven by $P_{comX}$ in CDM growth conditions. LMD9-Δblp::$P_{comX}$-luxAB derivatives were precultivated in M17-lactose medium. The cells of the precultures were harvested (5000 g, 9 minutes, 20° C.) and washed twice in CDM medium. The washed cells were used to inoculate CDM medium in order to obtain an optical density of 0.05 at 600 nm. A small volume of S. thermophilus cultures (300 μl) was then transferred in white microplate with a transparent bottom (655095; Greiner, Alphen a/d Rijn, The Netherlands) and grown at 37° C. Luminescence at 595 nm and optical density at 600 nm ($OD_{600}$) were recorded with the automatic Synergy HT multi-mode microplate reader. The luciferase activity catalysed by LuxAB requires the presence of nonanal as substrate. In this experiment, we supplied nonanal in a volatile form to the cultures by placing 50 μl of a solution containing 1% nonanal (Acros Organics ref. 204-688-5) diluted in mineral oil in the spaces between the wells of a covered microplate (11). The nonanal present in the solution will become volatile and there will be an equilibrium between the concentration of nonanal present in the air and in the culture samples. The luminescence and absorbance were scanned every 10 minutes during 6 hours. The maxima RLU/OD of the mutant strains were compared to those of the original strain. Deletion of the Rgg gene STER_0316 had a negative impact on LuxAB activity (LMD9-Δblp::$P_{comX}$-luxAB ΔSTER_0316::P32-cat mutant: results are represented on Table 1; for each assay, only the maximum RLU/OD value is indicated).

TABLE 1

Maximum luciferase activity of LMD9-Δblp::$P_{comX}$-luxAB derivatives cultivated in CDM

| Rgg-encoding genes deleted | Strain | Maximum luciferase activity (RLU/OD) |
|---|---|---|
| none | LMD9-Δblp::$P_{comX}$-luxAB | 9970 |
| STER_0316 | LMD9-Δblp::$P_{comX}$-luxAB ΔSTER_0316::P32cat | 103.8 |

Indeed, the maximum RLU/OD measured in strain LMD9-Δblp::$P_{comX}$-luxAB ΔSTER_0316::P32-cat was 96-fold lower than in the parental strain. These results indicate that the regulator STER_0316 is a key factor in the control of comX expression.

Since it was demonstrated that the deletion of STER_0316 dramatically reduces the transcription of comX, it was to be expected that competence in strain LMD9-Δblp::$P_{comX}$-luxAB ΔSTER_0316::P32-cat was also affected. Indeed, ComX is known as the main sigma factor responsible of the expression of the late competence genes.

For this experimental work, the transformation rates of strains LMD9-Δblp::$P_{comX}$-luxAB and LMD9-Δblp::$P_{comX}$-luxAB ΔSTER_0316::P32-cat were compared. Both strains are sensitive to erythromycin. The donor DNA was the plasmid pGIUD0855ery (FIG. 3). This plasmid is unable to replicate in S. thermophilus. It contains an operational erythromycin resistance gene ($P_{ery}$-ery) fused with the left and right ends of stu0855, a S. thermophilus gene from strain LMG18311. Assays were made in order to render strain LMD-9 resistant to erythromycin upon acquisition of $P_{ery}$-ery expression cassette.

Both strains were grown in 300 μL CDM in microplates, in the presence or not of added plasmid pGIUD0855ery. Preculture and cultures were performed as described above. In one set of experiment, 1 μg/mL of plasmid pGIUD0855ery was added to the culture in the same time as inoculation and in the second set of experiment no plasmid DNA was added. The cultures were grown during 6 hours and serial dilutions were plated on the surface of M17-lactose agar medium containing erythromycin. Table 2 below presents the results of the assays.

TABLE 2

Transformation rates of LMD9-Δblp::$P_{comX}$-luxAB derivatives grown in CDM upon addition or not of donor DNA (1 μg/mL)

| | transformation rate | |
|---|---|---|
| strain | Without added DNA | With addition of pGIUD0855ery |
| LMD9-Δblp::$P_{comX}$-luxAB | <$10^{-8}$ | $8 \times 10^{-5}$ |
| LMD9-Δblp::$P_{comX}$-luxAB ΔSTER_0316::P32-cat | <$10^{-8}$ | <$10^{-8}$ |

The results obtained with strain LMD9-Δblp::$P_{comX}$-luxAB show that erythromycin resistant clones were only obtained upon addition of plasmid pGIUD0855ery in the cultivation medium. Ten of the isolated clones were further analysed to localise the $P_{ery}$-ery gene. The integration of the $P_{ery}$-ery in all clones at the LMD-9 locus corresponding to stu0855 was demonstrated by PCR using primers Upstu0855 (5'-GGTATTGATCCCGAATTCAGATGTTTGTAG-3') (SEQ ID NO: 23) and Downstu0855 (5'-GGCTGGATG-GCATAACCGAGCTTTTGTTTC-3') (SEQ ID NO: 24). However, such erythromycin-resistant clones were not obtained in the strain deleted for STER_0316.

Altogether, the data from example 1 demonstrate that STER_0316 is an essential transcriptional activator of comX, that acts either directly by binding on comX promoter sequence or indirectly by stimulating the transcription of a second regulator. For this reason, STER_0316 is expected to be part of a Rgg regulator/signaling peptide system controlling competence induction in *S. thermophilus* LMD-9.

2. The Deletion of shp316 Impairs comX Induction and Natural Transformation in CDM The mature signaling peptides that interact with regulators of the Rgg family are generally hydrophobic and small. The peptides involved in the regulation of conjugation in *Enterococcus faecalis* and virulence in *Bacillus cereus* are synthesized as larger precursor peptides in the cytoplasm. They then undergo several maturation steps leading to the release of the active pheromone in the extracellular medium (8, 9).

The inventors identified a 75 bp-long ORF that was not annotated in the public sequence databases. The ORF is located 32 bp downstream of STER_0316 in the genome of *S. thermophilus* LMD-9 and was named shp316 (SHP for small hydrophobic peptide). The nucleotide sequence is the following:

```
                                        (SEQ ID NO: 6)
TTGAAAACCCTGAAAATATTTGTACTATTTTCACTACTTATTGCTATCTT

GCCTTATTTTGCAGGATGTCTTTAA.
```

In order to study the role of Shp316 in the control of comX induction and natural transformation in CDM, the inventors replaced shp316 of strain LMD9-Δblp::$P_{comX}$-luxAB by the chloramphenicol expression cassette P32-cat. The strategy followed to create strain LMD9-Δblp::$P_{comX}$-luxABΔ-shp316::P32-cat is the same as those described for strain LMD9-Δblp::$P_{comX}$-luxABΔSTER_0316::P32-cat (see example 1 and FIG. 6), using the following primers:

```
OL1:
                                        (SEQ ID NO: 25)
5'-TTGCTTAATGCTGTCTATCCAACTTATGACCGTATTCGC-3'

OL2:
                                        (SEQ ID NO: 26)
5'-CCTTATGGGATTTATCTTCCTTACAAAATATAACTCCTTTTAAC-3'

OL3:
                                        (SEQ ID NO: 27)
5'-TAAGGAAGATAAATCCCATAAGG-3'

OL4:
                                        (SEQ ID NO: 28)
5'-TTCACGTTACTAAAGGGAATGTA-3'

OL5:
                                        (SEQ ID NO: 29)
5'-TACATTCCCTTTAGTAACGTGAATAATAAGGAGCCATCATG-3'

OL6:
                                        (SEQ ID NO: 30)
5'-AAACTTCTTGAAGACAATTATTGGCTACCTTGGCTTGCTG-3'
```

The identity of the desired mutant is then PCR-checked with the primer pair Chshp316A (5'-TTGTTG-GACTTTCGCGTATTTATGTAGG-3') (SEQ ID NO: 31) and Chshp316B (5'-TTGAGTTGACCTTTTTCTTCCTTAT-TCAC-3') (SEQ ID NO: 32)

The impact of shp316 deletion on comX expression and on natural transformation was investigated by measuring the respective luminescence driven by $P_{comX}$ and natural transformation of strain LMD9-Δblp::$P_{comX}$-luxABΔshp316::P32-cat. The experimental procedures were the same as those described in example 1. Luminescence and absorbance were measured during growth of the strains in CDM at 37° C. (microplates). Natural transformation experiments were performed by growing the strains in presence of the plasmid pGIUD0855ery (1 μg). The identity of the erythromycin transformants are PCR-checked as described in example 1. The results are presented in the Table 3 below.

TABLE 3

Transformation rates and maximum luciferase activity of LMD9-Δblp::$P_{comX}$-luxAB derivatives cultivated in CDM. The competence experiments are performed with or without donor DNA (1 μg/mL)

| | Transformation rates | | |
|---|---|---|---|
| strain | Without added DNA | With addition of pGIUD0855ery | Maximum luciferase activity (RLU/OD) |
| LMD9-Δblp::$P_{comX}$-luxAB | <$10^{-8}$ | $4.4 \times 10^{-4}$ | 10535 |
| LMD9-Δblp::$P_{comX}$-luxABΔshp316::P32-cat | <$10^{-8}$ | <$10^{-8}$ | 97 |

The results of Table 3 show that the deletion of shp316 impairs comX induction in CDM. Indeed, the maximum RLU/OD measured in strain LMD9-Δblp::$P_{comX}$-htxABΔ-shp316::P32-cat is 109-fold reduced compared to strain LMD9-Δblp::$P_{comX}$-luxAB, and similar to that of strain LMD9-Δblp::$P_{comX}$-luxABΔSTER_0316::P32-cat (see Table 1). In addition, no erythromycin-resistant transformant could be obtained for strain LMD9-Δblp::$P_{comX}$-luxABΔ-shp316::P32-cat in our experiments. These results demonstrate that Shp316 is a major player in competence development in *S. thermophilus*.

3. The Over-Expression of shp316 Complements the Competence Defect of Strain LMD9-Δblp::$P_{comX}$-luxAB Δshp316::P32-cat In example 2, it was shown that strain LMD9-Δblp::$P_{comX}$-luxABΔshp316::P32-cat is unable to develop competence in CDM growing conditions. Since it cannot be excluded that this phenotype results from polar effects induced by the insertion of the chloramphenicol resistance cassette, competence complementation experiments of strain LMD9-Δblp::$P_{comX}$-luxABΔshp316::P32-cat were performed.

The inventors constructed a shp316-expression plasmid by cloning shp316 downstream of the constitutive P32 promoter in plasmid pMG36ET (6). The pMG36ET vector contains a replication origin that is functional in *S. thermophilus*, and encodes an erythromycin-resistance gene. The cloning strategy is the following: (i) shp316 ORF was PCR-amplified with primer pair pMGSHP316sur1 (5'-AGCTCTA-GATAAATAATAGTTAAAAGGAG-3') (SEQ ID NO: 33) and pMGSHP316sur2 (5'-TTTCTGCAGTTACATTTTG-GCATGATGGCTCC-3') (SEQ ID NO: 34) (ii) the PCR products and the plasmid pMG36ET were cut with the restriction enzymes XbaI and PstI, and (iii) ligated together. The obtained plasmid was named pMGSHP316. In a second step, plasmid pMGSHP316 was introduced by electroporation in strain LMD9-Δblp::$P_{comX}$-luxABΔshp316::P32-cat. The obtained strain was named LMD9-Δblp::P$_{comX}$-luxABΔ-shp316::P32-cat [pMGSHP316]. The empty pMG36ET plasmid was also introduced by electroporation in strains LMD9-Δblp::P$_{comX}$-luxABΔshp316::P32-cat and LMD9-Δblp::P$_{comX}$-luxAB. Finally, the inventors studied the effect of shp316 over-expression on the competence phenotype of strain LMD9-Δblp::P$_{comX}$-luxABΔshp316::P32-cat. For this purpose, the LuxAB activity and transformation rates of strains LMD9-Δblp::P$_{comX}$-luxAB [pMG36ET], LMD9-Δblp::P$_{comX}$-luxABΔshp316::P32-cat [pMG36ET] and LMD9-Δblp::P$_{comX}$-luxABΔshp316::P32-cat [pMGSHP316] were compared. The experimental procedure was the same as those described in examples 1 and 2, except that the donor DNA used is the plasmid pGIDUDrpsl. This plasmid is unable to replicate in *S. thermophilus* and contains a 3.8 kb-fragment encoding a mutated rpsL gene conferring resistance to streptomycin. Assays were made in order to render LMD-9 resistant to streptomycin upon acquisition of the mutated rpsL gene.

TABLE 4

Transformation rates and maximum luciferase activity of LMD9-Δblp::P$_{comX}$-luxAB derivatives cultivated in CDM containing erythromycin. The competence experiments are performed with or without donor DNA (1 μg/mL)

| Strain | Transformation rates | | Maximum luciferase activity (RLU/OD) |
|---|---|---|---|
| | Without added DNA | With addition of pGIUDrpsl | |
| LMD9-Δblp::P$_{comX}$-luxAB [pMG36ET] | <10$^{-8}$ | 3.2 × 10$^{-4}$ | 9980.3 |
| LMD9-Δblp::P$_{comX}$-luxABΔshp316::P32-cat [pMG36ET] | <10$^{-8}$ | <10$^{-8}$ | 87.2 |
| LMD9-Δblp::P$_{comX}$-luxABΔshp316::P32-cat [pMGSHP316] | <10$^{-8}$ | 2.4 × 10$^{-4}$ | 9032.1 |

The results of Table 4 show that plasmid pMGSHP316 complements almost completely the phenotype of strain LMD9-Δblp::P$_{comX}$-luxABΔshp316::P32-cat. Indeed, the maximum RLU/OD and transformation rate are in the same range of those measured in strain LMD9-Δblp::P$_{comX}$-luxAB [pMG36ET]. These experiments demonstrate unequivocally that the competence defect of strain LMD9-Δblp::P$_{comX}$-luxABΔshp316::P32-cat is due to the deletion of shp316.

4. Addition of Synthetic Peptides Derived from Shp316 in the Extracellular Medium Restores the Competence Defect of Strain LMD9-Δblp::P$_{comX}$-luxAB Δshp316::P32-cat The results from examples 2 and 3 strongly suggest that Shp316 is the precursor of the pheromone responsible for comX induction and natural transformation in *S. thermophilus*. Shp316, MKTLKIFVLFSLLIAILPYFAGCL (SEQ ID NO:1), displays the characteristics of signal sequences from lipoproteins (between 20 and 25 amino acids, positively-charged N-terminal end and an hydrophobic core). Interestingly, the conjugation pheromones of *E. faecalis* are also part of the signal sequences of lipoproteins. All mature conjugation peptides identified to date correspond to the hydrophobic core of lipoprotein signal sequences (9).

To test the hypothesis that Shp316 is matured and released in the medium to act as a competence pheromone, supplementation experiments of the competence defect of strain LMD9-Δblp::P$_{comX}$-luxABΔshp316::P32-cat were carried out. For this purpose, a series of synthetic peptides corresponding to different fragments of Shp316 were tested for their ability to induce competence (see table 5).

The experimental strategy is described below. Strain LMD9-Δblp::P$_{comX}$-luxABΔshp316::P32-cat is precultivated in M17-lactose medium. The cells of the preculture were harvested (5000 g, 9 minutes, 20° C.) and washed twice in CDM and then resuspended in CDM. The washed cells are diluted in fresh CDM to obtain an optical density of 0.05 at 600 nm, and then incubated at 37° C. After 1.5 h of incubation, in one set of experiment, 1 μM of one of the tested synthetic peptides and 1 μg/mL of pGIUD0855ery were added to the culture; whereas 1 μg/mL of pGIUD0855ery but no synthetic peptide was added to the second set of experiment. The cultures were grown during 6 hours and serial dilutions were plated on the surface of M17-lactose agar medium containing 2.5 μg/mL of erythromycin to measure transformation efficiency. Results are reported in table 5.

Out of the 10 synthetic peptides that were tested, 4 peptides (PYFAGCL (SEQ ID NO: 91), LPYFAGCL (SEQ ID NO: 92), ILPYFAGCL (SEQ ID NO: 93) and AILPYFAGCL (SEQ ID NO: 94)) allowed to restore the competence defect of strain LMD9-Δblp::P$_{comX}$-luxABΔshp316::P32-cat. Interestingly, all these 4 peptides contain the carboxy-terminal part of Shp316. It is also noticeable that in the absence of the carboxy-terminal leucine of Shp316 none of the synthetic peptides has an ability to restore the competence defect of LMD9-Δblp::P$_{comX}$-luxABΔshp316::P32-cat.

TABLE 5

Transformation rate of LMD9-Δblp::P$_{comX}$-luxABΔshp316::P32-cat with 1 μg/mL of pGIUD0855ery upon addition or not 1 μM of different synthetic peptides

| | Transformation rate | |
|---|---|---|
| Added peptide | Without peptide addition | With peptide addition |
| ILPYFAG (SEQ ID NO: 90) | <10$^{-8}$ | <10$^{-8}$ |
| PYFAGCL (SEQ ID NO: 86) | <10$^{-8}$ | 4.78 × 10$^{-3}$ |
| LPYFAGCL (SEQ ID NO: 85) | <10$^{-8}$ | 3.18 × 10$^{-3}$ |
| ILPYFAGCL (SEQ ID NO: 84) | <10$^{-8}$ | 3.42 × 10$^{-3}$ |
| AILPYFAGCL (SEQ ID NO: 83) | <10$^{-8}$ | 2.21 × 10$^{-3}$ |
| PYFAGC (SEQ ID NO: 91) | <10$^{-8}$ | <10$^{-8}$ |
| LPYFAGC (SEQ ID NO: 92) | <10$^{-8}$ | <10$^{-8}$ |
| ILPYFAGC (SEQ ID NO: 93) | <10$^{-8}$ | <10$^{-8}$ |
| AILPYFAGC (SEQ ID NO: 94) | <10$^{-8}$ | <10$^{-8}$ |
| PYFAG (SEQ ID NO: 95) | <10$^{-8}$ | <10$^{-8}$ |

Ability of peptides derived from Shp316 to restore the competence defect of LMD9-Δblp::P$_{comX}$-luxABΔshp316::P32-cat was further investigated focusing on the synthetic peptide PYFAGCL. Experimental work was performed as described above except that various concentrations of PYF-AGCL were used: 0 nM, 1 nM, 10 nM, 100 nM, 500 nM, 1 µM, 2.5 µM and 5 µM. Results are presented in table 6.

TABLE 6

Transformation rate of LMD9-Δblp::$P_{comX}$-luxABΔshp316::P32-cat with 1 µg/mL of pGIUD0855ery upon addition of various concentration of the synthetic peptide PYFAGCL (SEQ ID NO: 86)

| Added concentration of PYFAGCL (SEQ ID NO: 86) (in nM) | Transformation rate |
|---|---|
| 0 | <$10^{-8}$ |
| 1 | <$10^{-8}$ |
| 10 | <$10^{-8}$ |
| 100 | $4.14 \times 10^{-7}$ |
| 500 | $1.01 \times 10^{-3}$ |
| 1000 | $5.15 \times 10^{-3}$ |
| 2500 | $3.10 \times 10^{-3}$ |
| 5000 | $6.38 \times 10^{-3}$ |

Results show that there is a dose-response of the amount of this peptide, which is typical of pheromone-regulated systems. Indeed, concentrations of PYFAGCL (SEQ ID NO: 86) lower than 100 nM did not restore the competence of LMD9-Δblp::$P_{comX}$-luxABΔshp316::P32-cat; while response was almost exponential from 100 nM and 500 nM. Maximum efficiency of the peptide was recorded for a concentration of 1 µM. Transformation efficiency of LMD9-Δblp::$P_{comX}$-luxABΔshp316::P32-cat then reached a plateau, indicating saturation of the peptide induction.

5. Addition of Synthetic Peptides Derived from Shp316 in the Extracellular Medium Supplements the Competence Defects of Strains *S. thermophilus* LMG18311, *S. thermophilus* CNRZ1066 and *Streptococcus salivarius* JIM8777.

Genes that were shown to be essential for competence induction and natural transformation in CDM conditions are also present in the genome of strains LMG18311 and CNRZ1066. However, in contrast to strain LMD-9, competence induction is less efficient in strain LMG18311 grown in CDM, and no competence induction is observed in the case of strain CNRZ1066. As well we were unable to induce natural competence in CDM medium of *S. salivarius* JIM8777, a species that is closely related to *S. thermophilus*. We tested the ability of the peptides of the invention to improve the transformation rates of these strains by adding 1 µM of peptide derive from Shp316 in their culture medium.

Similarly to the protocol used in example 4, strains LMD-9, LMG18311, CNRZ1066 and JIIVI8777 were pre-cultivated in M17-lactose medium. The cells of the precultures were harvested (5000 g, 9 minutes, 20° C.) and washed twice in CDM and then resuspended in CDM. The washed cells were diluted in fresh CDM medium to obtain an optical density of 0.05, and then incubated at 37° C. After 1.5 h of incubation, in one set of experiment, 1 µM of one of the tested synthetic peptides and 1 µg/mL of pGIUD0855ery DNA (in case of *S. thermophilus* strains), or 1 µg/ml of pG+host09 DNA (in case of *S. salivarius* strains) were added to the culture, whereas 1 µg/mL of DNA but no synthetic peptide was added to the second set of experiment. The cultures were grown during 6 hours and serial dilutions were plated on the surface of M17-lactose agar medium containing 2.5 µg/mL of erythromycin to measure transformation efficiency. Transformed *S. thermophilus* and *S. salivarius* cells are selected at 37° C. and 29° C., respectively. Results are reported in table 5.

Results showed that the extracellular addition of the PYF-AGCL (SEQ ID NO: 86) in CDM has some but little effect (10-fold increase) on the natural competence of the strain LMD-9. However for the strain that is poorly inducible in CDM, LMG18311, the efficiency of transformation is significantly increased (1000-fold increase). And more importantly, addition of PYFAGCL (SEQ ID NO: 86) complements the transformation defect in CDM of CNRZ1066 and JIM8777.

TABLE 7

Transformation rate of various strains with 1 µg/mL of pGIUD0855ery (in case of *S. thermophilus*) or pG+host9 (in case of *S. salivarius*) upon addition or not of 1 µM of the synthetic peptide PYFAGCL

| | Transformation rate | |
|---|---|---|
| Strains | Without peptide addition | With peptide addition |
| *S. thermophilus* LMD-9 | $4.46 \times 10^{-4}$ | $3.10 \times 10^{-3}$ |
| *S. thermophilus* LMG18311 | $2.08 \times 10^{-7}$ | $3.17 \times 10^{-4}$ |
| *S. thermophilus* CNRZ1066 | <$10^{-8}$ | $3.69 \times 10^{-4}$ |
| *S. salivarius* JIM8777 | <$10^{-8}$ | $3.07 \times 10^{-6}$ |

In this context, analysis of the recently available genome sequence of *S. salivarius* SK126 allowed the identification of a locus strongly homologous to STER_0316 and shp316 genes of *S. thermophiles*. The peptide deduced from the gene equivalent to shp316 in *S. salivarius* SK126 slightly differs from that of Shp316. To take these differences into account, the experimental work described above was duplicated but using the following synthetic peptide: PYFTGCL (SEQ ID NO: 128). This peptide differs from the peptide previously used by a single conservative modification that consists in the replacement of the alanine residue in position 4 by a threonine residue. The results are displayed in Table 8. Despite the presence of the threonine residue in position 4, PYFTGCL (SEQ ID NO: 128) is also able to complement the transformation defect in CDM of CNRZ1066 and JIM8777.

TABLE 8

Transformation rate of various strains with 1 µg/mL of pG+host09 upon addition or not of 1 µM of the synthetic peptide PYFTGCL (SEQ ID NO: 128)

| | Transformation rate | |
|---|---|---|
| Strains | Without peptide addition | With peptide addition |
| *S. thermophilus* CNRZ1066 | <$10^{-8}$ | $3.48 \times 10^{-7}$ |
| *S. salivarius* JIM8777 | <$10^{-8}$ | $5.77 \times 10^{-7}$ |

6. A Synthetic Peptide Derived from Shp316 is able to Induce Natural Competence in Many *S. thermophilus* Strains.

In order to show that the system of competence induction is ubiquitous to *S. thermophilus*, we tested the ability of the peptides of the invention to improve the transformation rates of multiple strains by adding 1 µM of peptide derived from Shp316 in their culture medium.

Similarly to the protocol used in example 4, various *S. thermophilus* strains, including LMD-9, CNRZ1066 and LMG18311 used as controls, were pre-cultivated in M17-lactose medium. The cells of the precultures were harvested (5000 g, 9 minutes, 20° C.) and washed twice in CDM and then resuspended in CDM. The washed cells were diluted in fresh CDM medium to obtain an optical density of 0.05, and then incubated at 37° C. After 1.5 h of incubation, in one set of experiment, 1 µM of one of the tested synthetic peptides (LPYFAGCL) (SEQ ID NO: 85) and 1 µg/mL of pGIUD0855cat DNA were added to the culture, whereas 1 µg/mL of DNA but no synthetic peptide was added to the second set of experiment. Plasmid pGIUD0855cat is a pUC18-derivative containing a chloramphenicol resistance cassette flanked by 1-kb fragments corresponding to the upstream and downstream regions of stu0855. Upon transformation, it promotes the genetic replacement of stu0855 by P32-cat through homologous recombination (FIG. 7). The cultures were grown during 6 hours and serial dilutions were plated on the surface of M17-lactose agar medium containing 5 µg/mL of chloramphenicol to measure transformation efficiency. Transformed *S. thermophilus* cells were selected at 37° C.; when transformants were obtained, the transformation efficiency was calculated and is given in Table 9.

TABLE 9

Transformation rate of various *S. thermophilus* strains with 1 µg/mL of pUC18_stu0855::P32cat upon addition or not of 1 µM of the synthetic peptide LPYFAGCL (SEQ ID NO: 85)

| Strains | Transformation rate | |
|---|---|---|
| | Without peptide addition | With peptide addition |
| S. thermophilus LMD-9 | $1.7 \times 10^{-3}$ | $5.4 \times 10^{-3}$ |
| S. thermophilus LMG18311 | $3.4 \times 10^{-6}$ | $1.3 \times 10^{-1}$ |
| S. thermophilus CNRZ1066 | $<10^{-8}$ | $3 \times 10^{-2}$ |
| S. thermophilus DGCC715 | $<10^{-8}$ | $1.2 \times 10^{-2}$ |
| S. thermophilus DGCC782 | $<10^{-8}$ | $2 \times 10^{-3}$ |
| S. thermophilus DGCC3367 | $4.7 \times 10^{-7}$ | $1.8 \times 10^{-3}$ |
| S. thermophilus DGCC7666 | $1.8 \times 10^{-6}$ | $4.2 \times 10^{-2}$ |
| S. thermophilus DGCC7694 | $<10^{-8}$ | $3.9 \times 10^{-2}$ |
| S. thermophilus DGCC7710 | $6.8 \times 10^{-7}$ | $1 \times 10^{-2}$ |
| S. thermophilus DGCC7773 | $<10^{-8}$ | $1.5 \times 10^{-1}$ |
| S. thermophilus DGCC7785 | $<10^{-8}$ | $4.1 \times 10^{-5}$ |
| S. thermophilus DGCC7790 | $<10^{-8}$ | $4.3 \times 10^{-2}$ |
| S. thermophilus DGCC7796 | $3.1 \times 10^{-6}$ | $6.9 \times 10^{-2}$ |
| S. thermophilus DGCC7809 | $<10^{-8}$ | $5.8 \times 10^{-4}$ |
| S. thermophilus DGCC7853 | $2.2 \times 10^{-4}$ | $4.9 \times 10^{-4}$ |
| S. thermophilus DGCC7854 | $1.1 \times 10^{-7}$ | $5.3 \times 10^{-3}$ |
| S. thermophilus DGCC7879 | $8.1 \times 10^{-7}$ | $8.6 \times 10^{-3}$ |
| S. thermophilus DGCC7891 | $<10^{-8}$ | $1.4 \times 10^{-4}$ |
| S. thermophilus DGCC7909 | $<10^{-8}$ | $4.5 \times 10^{-3}$ |

The results for the transformation experiment realised in CDM without the peptide indicate that only 9 were competent for natural transformation with a transformation frequency between $10^{-4}$ and $10^{-7}$. In contrast when the CDM is supplemented with LPYFAGCL (SEQ ID NO: 85) peptide, 19 strains were competent. Advantageously, for 17 strains out of these 19 competent strains, the efficiency of transformation was greatly improved by the addition of the peptide; up to 6 Log.

7. Use of Induced Natural Competence to Improve the Acidifying Properties of Strain CNRZ1066

The fast acidifying properties of *S. thermophilus* strains depends on the activity of the cell-wall protease PrtS (13). PrtS hydrolyses milk caseins into smaller peptides, which can next be imported through specific transporters into the cells. Thus, PrtS ameliorates the growth of *S. thermophilus* in milk, improving their ability to produce lactic acid that acidifies the milk.

The FSDA (Fast Strain Differentiating Agar) is a well known solid milk-based medium on which fast and slow acidifying strains can easily be distinguished; colonies of the first type appear large and white, while colonies of the second type are small and translucent (14). LMD-9 is a fast acidifying *S. thermophilus* strain that was shown to possess a prtS gene. In this strain, the prtS gene (STER_0846) is located in a chromosomal region that is flanked by genes ciaH (STER_0839) and rpsT (STER_0850) (Accession number CP000419 (15)). On FSDA medium LMD-9 colonies appears big and white. On the contrary, CNRZ1066 is a slow-acidifying strain forming small and translucent colonies on FSDA. CNRZ1066 does not contain any prtS gene, neither between ciaH and rpsT genes, nor anywhere else on its chromosome (16).

Experimental work was performed in order to transfer the prtS gene from LMD-9 to CNRZ1066 through the induction of natural competence using the synthetic peptide PYFAGCL. First, a DNA fragment encompassing the whole 16 kb prtS locus from LMD-9 was amplified by PCR using primer STER_0839 (5'-AATCTTTGATCGTTTCTACCGAGTAGAC-3') (SEQ ID NO: 35) and STER_0850 (5'-TAACTAATCGAAAACTCCAGTAGGAG-3') (SEQ ID NO: 36). Then, similarly to what was done in example 5, strain CNRZ1066 was pre-cultivated in M17-lactose medium. The cells of the precultures were harvested (5000 g, 9 minutes, 20° C.) and washed twice in CDM and then resuspended in CDM. The washed cells were diluted in fresh CDM medium to obtain an optical density of 0.05, and then incubated at 37° C. After 1.5 hour of incubation, 1 µM of PYFAGCL synthetic peptide and 1.6 µg/mL of the PCR-amplified prtS locus were added to the culture. The culture was grown during 6 hours and serial dilutions were plated on the surface of FSDA in order to have about $10^5$ colonies per plate. Following a 24-hour incubation at 37° C., the plates were investigated for the presence of large white colonies in the background of small translucent colonies.

Three colonies of this type were isolated and cultivated in M17 medium at 37° C. In order to control the presence of the prtS gene in these 3 isolates, their genomic DNA was extracted and submitted to a prtS-specific PCR using primers PrtS1 (5'-AAAGAGCTCAATAAATGAAGGAGAAAAACTAGG-3') (SEQ ID NO: 37) and PrtS2 (5'-AAAGTCGACAACTTGTGATAAAGCTAGTGTTGG-3') (SEQ ID NO: 38). For all 3 isolates, a specific prtS DNA fragment of 2.7 kpb was amplified, demonstrating the presence of the prtS gene in their genome.

Acidification properties of a strain can be characterized by its kinetic of acidification of milk and more specifically by its maximum speed of acidification. Classically, the kinetic of acidification is measured by monitoring the change of pH over time and the maximum speed of acidification can be calculated from this kinetic. The CINAC is an apparatus that is extensively used in the dairy industry to measure acidification kinetics of lactic acid bacteria. The CINAC automated system is described in (17).

One of the isolate named CNRZ1066prtS was further analysed for its kinetic of acidification comparatively to CNRZ1066. Kinetics of acidification can be described by: i) the time to reach a certain pH, ii) the maximum speed of acidification Vm (pH Unit/min) that is the maximum value of the derived pH curve, and the duration of the lag phase of acidification Ta (min) that is time to obtain a pH reduction of 0.08 pHU. CNRZ1066 and CNRZ1066prtS were pre-cultivated overnight in milk (10% (w/v) skim milk powder dissolved in distilled water then autoclaved for 20 min at 110° C.). The pre-cultures were used to inoculate at 1% (w/v) 100 ml of milk then incubated at 42° C. The evolution of pH over time was monitored using a CINAC device (Ysebaert, France)

The CINAC curves are displayed in FIG. 7. Comparatively to CNRZ1066, CNRZ1066prtS displayed a different kinetic of acidification. The Ta is shorter by 27 min (68 min compare to 95 min). The time to reach pH 4.5 is shorter by 610 min (310 min compare to 920 min). Finally, the calculated Vm is faster for CNRZ1066prtS (−0.0162 pHU/min) than for CNRZ1066 (−0.0070 pHU/min). This shows the benefit for a strain to acquire prtS in order to increase its speed of acidification of milk.

8. Use of Induced Natural Competence to Modify the Nutritional Requirement of LMD-9

In silico analyses have shown that strain LMG18311 contained all genes necessary for the biosynthesis of all amino acids with the exception of histidine for which only hisK, a putative histidinol-phosphatase, is present (Hols et al., 2005, (1)). This result is in contrast with the presence of a complete his gene cluster in the LMD-9 genome (Hols et al., 2005, (1)).

The genetic organisation of the his locus of LMD-9 strain (FIG. 9A) is composed of ten genes (7.3 kb; STER__1198 to STER__1207) organised in a putative operon and followed by hisK (STER__1212) located 3.3 kb downstream. These two regions are separated by three genes (STER__1208, STER__1210, and STER__1211) and a truncated transposase (pseudogene, STER__1209). STER__1210 codes for a protein potentially involved in EPS biosynthesis and the two others (STER__1208 and STER__1211) code for uncharacterised proteins. On the 5' end, the operon is flanked by rodA (STER__1197), which codes for a protein implicated in the cell division. RodA, STER__1210 and STER__1211 share an identity reaching 99% with their homologues present on the LMG18311 genome (STU__1229, STU__1230 and STU1231; FIG. 9B).

To delete the histidine operon from LMD-9, we have applied the cre-lox-based system for gene deletion described for *Lactobacillus plantarum* (18). This strategy is divided in three steps: 1) Replacement of the target his genes by a P32-cat cassette surrounded by lox sites 2) Removal of the P32-cat cassette by site-specific recombination with the Cre recombinase 3) Curing of the cre-expression vector.

To build the DNA fragment necessary to remove the his operon from the LMD-9 chromosome, three individual PCR reactions were performed to amplify fragments A, B and C (FIGS. 9 and 10). Fragment A corresponds to the upstream region of the his operon. Fragment A is amplified with the primer pair UpDelHis1/UpDelHis2. Fragment B corresponds to the chloramphenicol expression cassette P32-cat and is amplified with primer pair Uplox66/DNlox71 from the pNZ5319 vector. Fragment C corresponds to the downstream region of the gene of interest and is amplified with the primer pair DNDelHis1/DNDelHis2. The sequence of Uplox66 and DNlox71 are respectively complementary to the 5' end of UpDelHis2 and 5' end of DNDelHis1 and their association creates two different lox sites, lox66 and lox71. The three PCR products, A, B and C, were then mixed in equimolar concentration and an overlapping PCR were performed with the primer pair UpDelHis1/DNDelHis2 to join fragments A, B and C together (FIG. 10).

The following primers were used:

```
UpDelHis1:
                                          (SEQ ID NO: 39)
5'-TTATGTCTTGGCCCTTGTCAAGGATTTGGG-3'

UpDelHis2:
                                          (SEQ ID NO: 40)
5'-CCTTATGGGATTTATCTTCCTTATTCAATCTTTCGTAATCCTTT-3'

DNDelHis1:
                                          (SEQ ID NO: 41)
5'-TACATTCCCTTTAGTAACGTGAAAAAGCAATGTTCATGACC-3'
```

-continued
```
DNDelHis2:
                                          (SEQ ID NO: 42)
5'-TTTACTAGTCCCAGATGCACGCATACGACG-3'

Uplox66:
                                          (SEQ ID NO: 43)
5'-TAAGGAAGATAAATCCCATAAGG-3'

DNlox71:
                                          (SEQ ID NO: 44)
5'-TACATTCCCTTTAGTAACGTGAA-3'
```

The overlapping PCR product was transferred through natural competence in strain LMD-9. Similarly to the protocol used in example 4, strain LMD-9 was pre-cultivated in M17-lactose medium. The cells of the precultures were harvested (5000 g, 9 minutes, 20° C.) and washed twice in CDM and then resuspended in CDM. The washed cells were diluted in fresh CDM medium to obtain an optical density of 0.05, and then incubated at 37° C. After 1.5 hour of incubation, 1 µM of LPYFAGCL (SEQ ID NO: 85) synthetic peptide and 1 vg/mL of the PCR product prepared above (joining the A, B and C fragments) were added to the culture. After the DNA uptake by the bacteria, the P32-cat cassette flanked by the two lox sites spontaneously replaces the his operon by double homologous recombination (FIG. 10). The transformation rate of the overlapping PCR was $1.1 \times 10^{-6}$ (160 Chloramphenicol-resistant CFU/mL). One isolate named CB15 was selected. Correct integration was confirmed by PCR/restriction using the CKDelHis1/CKDelHis2 primers and the NcoI endonuclease The following primers were used: CKDelHis1: 5'-TTGATGATGAGGTGGCTGATATGGACAAGG-3' (SEQ ID NO: 45) and CKDelHis2: 5'-TTAGACCCTTTAC-GACGCTTGCCTTGG-3' (SEQ ID NO: 46). Auxotrophy of CB 15 for histidine was confirmed (not shown).

The lox66-P32cat-lox71 cassette can then be removed and transformed into a single in-frame lox72 site by using the site-specific Cre recombinase (FIG. 11). Recombination between the lox71 and the lox66 mutant creates the loxP double mutant site lox72, which has a strongly reduced affinity for the Cre recombinase, and thus avoid the re-introduction of the cassette.

The erythromycin-selectable Cre expression vector was transferred through natural competence in CB15 (as described above). The transformation rate of the pGhostCre vector was $1.7 \times 10^4$ (27000 Erythromycin-resistant CFU/ml). 50 Ery$^R$ colonies were analysed on M17L containing Chloramphenicol and 96% were Cm$^S$ indicating the excision of cat. Deletion of the target loci was then verified by PCR using the following primers: CKDelHis3: 5'-TAAGTTG-GAGTATGCTGTTGGTCGTGTGGACGC-3' (SEQ ID NO: 47) and CKDelHis4: 5'-TTATCTTTAGCCTTGACCAAT-TCTTGTGAGGCC-3' (SEQ ID NO: 48) on 43 isolated colonies. All show the P32-cat excision. One was selected and designated CB2. The Cre expression vector was allowed to be lost spontaneously by culturing CB2 without selective pressure at 37° C. Upon 4 sub-cultures in M17 medium then plating on M17 agar medium, 32 colonies were selected and tested sensitive to erythromycin. The loss of the plasmid was controlled by PCR using the following primers: PGhost1: 5'-TTTATGCGTGAGAATGTTACAGTCTA-3' (SEQ ID NO: 49) and PGhost2: 5'-TGTAAATTTGGAAAGTTA-CACGTTAC-3' (SEQ ID NO: 50) and was confirmed for 84% of them. One isolate designated LMD-9deltaHis was selected for further analysis.

The growth of LMD-9deltaHis was tested in 300 µl CDM and CDM deprived of histidine at 37° C. Growth was monitored at 20-minutes intervals in the Varioskan Flash multi-mode reader (ThermoFisher Scientific, Zellic, Belgium). The results are presented in FIG. 12. In CDM, no significant difference was observed between LMD-9 and the his mutant. On the contrary, in the medium deprived of histidine, the growth of LMD-9deltaHis was totally abolished whereas the parental strain presented a normal growth curve.

9. Use of Induced Natural Competence and PCR-Amplified DNA to Modify the Nutritional Requirement of LMG18311

In order to modify the nutritional requirement of LM18311, the his operon from LMD-9 was transferred to the genome of LMG18311 using a DNA fragment amplified from LMD-9 chromosome. Selection of the modified cells was performed on a CDM agar deprived of histidine.

The his operon (13 kb) from LMD-9 was amplified by PCR using primers UpDelHis1 (5'-TTATGTCTTGGCCCTTGT-CAAGGATTTGGG-3') (SEQ ID NO: 39) and DNDelHis2 (5'-TTTACTAGTCCCAGATGCACGCATACGACG-3') (SEQ ID NO: 42) (see FIG. 9A). The transformation rate of the PCR product containing the histidine operon was 4.9× 10$^{-6}$ (30 CFU/mL on CDM without histidine). Insertion position of the his locus was verified for 6 isolates by PCR using the following primer pairs

```
CKDelHis3
                                    (SEQ ID NO: 47)
(5'-TAAGTTGGAGTATGCTGTTGGTCGTGTGGACGC-3')

UpDelHis2
                                    (SEQ ID NO: 40)
(5'-CCTTATGGGATTTATCTTCCTTATTCAATCTTTCGTAATCCTTT-
3')

CKDelHis4
                                    (SEQ ID NO: 48)
(5'-TTATCTTTAGCCTTGACCAATTCTTGTGAGGCC-3')

DNDelHis1
                                    (SEQ ID NO: 41)
(5'-TACATTCCCTTTAGTAACGTGAAAAAGCAATGTTCATGACC-3').
```

Four out of the 6 clones carried the histidine operon into their genome at the expected position. One of the clones, designated LMG18311::His, was selected. The integrity of the his operon was verified by PCR using the following primer pair: InDelHis1: 5'-CTACCGAGTTAACAGCGGT-TGGTTGGGC-3' (SEQ ID NO: 57) and InDelHis2: 5'-TTG-GTCCTCAAAACCAGCCTCCAACTG-3' (SEQ ID NO: 58) (see FIG. 9A). LGM18311::His was grown in 300 µl CDM and in CDM without histidine at 37° C. comparatively to LMG18311. Growth was monitored at 20-minutes intervals in the Varioskan Flash multi-mode reader (ThermoFisher Scientific, Zellic, Belgium). The results are presented in FIG. 13. In CDM, no significant difference of growth was observed between LMG18311 and the modified clone. However, in the CDM without histidine, no increase of OD was measured for the wild type strain LMG18311 WT. Conversely, LMG18311::His growth in the CDM deprived of histidine was similar to that in the plain CDM; thus proving the beneficial effect of the acquisition of the histidine operon on nutritional requirements of LMG18311.

10. Use of Induced Natural Competence and Chromosomal DNA Extracts to Modify the Nutritional Requirement of LMG18311

Similarly to what was done in example 9, induced natural competence was used to transfer to LMG18311 the genetic elements conferring to LMD-9 the ability to synthesize histidine. However instead of using a specific and enzymatically-synthesized DNA, the whole genome extracted from LMD-9 is used as genetic material for the transfer.

Natural competence was induced as described in previous examples using the LPYFAGCL peptide. Forty six µg of LMD-9 DNA was used and transformants were selected on CDM agar deprived of histidine. Calculated efficiency of transformation was 1.6×10$^{-4}$/µg. The presence of the histidine operon (or part of it) in the genome of some isolates was further confirmed by PCR analysis using the primer pair InDelHis1/InDelHis2 (see FIG. 9A). Nine isolates were found positive; they were named CL1, CL2, CL3, CL4, CL5, CL6, CL7, CL8 and CL9). To verify the functionality of the histidine operon inserted in their genome, the isolates were tested for their ability to grow in CDM without histidine at 37° C. using an automatic multi-mode reader. The results presented on FIG. 14 show dissimilar growth curves from one isolate to another. Since no disparity was observed for the growth of the three isolates obtained when the his-PCR was used as the transforming DNA (example 9, not shown), one can hypothesize that other genetic modification had occurred in these isolates upon transformation using LMD-9 total genomic DNA. To check for the possibility of multiple DNA transfer in these isolates, 5 PCRs specific of various chromosomal regions of LMD-9 were performed. The specific-PCRs targeted: i) prtS (using the primer pair STER_0847/SeqPRT-SII); ii) STER_1299 (ChSTER1299A/ChSTER1299B); iii) STER_1684 (ChSTER1684A/ChSTER1684B), iv) STER_0136 (ChSTER0136A/ChSTER0136B) and v) STER_0657 (ChSTER0657A/ChSTER0657B). Interestingly, the presence of prtS was detected in CL1 and CL2 genomes. As well, CL6 was positive to the STER_0657 specific-PCR. All other PCRs were found negative.

This example showed the possibility to transfer simultaneously genes from different loci (for example the his locus together with the prtS locus) by the induction of natural competence and the use of genomic DNA. As well, it opens the door to the transfer of very large DNA fragments (up to 100 kb or even more; that can not be enzymatically synthesized by PCR) directly obtained from a bacterial cell by extracting its whole genomic DNA.

The following primers were used for the 5 specific PCR:

```
                                    (SEQ ID NO: 59)
STER_0847:  5'-TAGTTTCTCAGAGATAGACTTTGG-3'

(SEQ ID NO: 60)
SeqPRTS11:  5'-TTTACCTCGTCCAGTCACTTTGCAAGC-3'

(SEQ ID NO: 61)
ChSTER1684A:5'-TTTACTATCATGTCATCATTTACAATAGG-3'

(SEQ ID NO: 62)
ChSTER1684B:5'-ATTTCTGTTAAATCCTGAGACATATCC-3'

(SEQ ID NO: 63)
ChSTER1299A:5'-TTAAGCCAACTGAACTTGACGCTATTGG-3'

(SEQ ID NO: 64)
ChSTER1299B:5'-AAATCTGTTGTATGCTGTAAAATATACTC-3'

(SEQ ID NO: 65)
ChSTER0136A:5'-TTTACAATATTTTTTGGTATCATTGCAG-3'

(SEQ ID NO: 66)
ChSTER0136B:5'-AAAAACTGCCAAATCTCCAATCTAGTCC-3'

(SEQ ID NO: 67)
ChSTER0657A:5'-AATATCGCTTTGGACACTTGTAGC-3'

(SEQ ID NO: 68)
ChSTER0657B:5'-TTCCAATTCAACATTGTACTCACG-3'
```

Annex I.

A—Preparation of Chemically Defined Medium (CDM)

In 860 mL of freshly prepared growing buffer. Add:
- 10 mL 100× vitamin solution (defrost one 11 mL-vitamin aliquot)
- 10 mL 100× metal solution (defrost one 40 mL-metal aliquot)
- 20 mL of freshly prepared 50×DNA precursor mix
- 100 mL 10× amino acids solution (defrost three 40 mL-aa aliquot)
- Mix by stirring and check that every component is dissolved
- bring the pH up to 6.6 with HCl 32%
- Filter-sterilize using 0.2 micron filters
- Wrap the 1 L-bottle in aluminium foil and keep at 4° C. The medium can be kept for maximum 2 weeks at 4° C.

B—Buffers and Solutions for the CDM

Growing buffer composition (volume: 1 L). Prepare fresh solution every time

| | |
|---|---|
| 1. lactose monohydrate (VWR 24945.291) | 10 g |
| 2. sodium acetate (Sigma S7545-250G) | 1 g |
| 3. citric acid triammonium salt (Sigma A1332-100G) | 0.6 g |
| 4. $KH_2PO_4$ (VWR 26936.293) | 3 g |
| 5. $K_2HPO_4$ (Merck 1.05104.1000) | 2.5 g |
| 6. urea (Merck) | 0.24 g |
| 7. L-tyrosine (Sigma T3754-100G) | 0.29 g |
| 8. L-ascorbic acid (Sigma A5960-100G) | 0.5 g |

Add 800 mL MilliQ water. Heat the solution (max. temperature: 40° C.). Bring the pH to 6.8-7 to dissolve all the components Bring the volume up to 860 mL with milliQ water. Prepare fresh solution every time Vitamin solution 100× (volume: 1 L)

| | |
|---|---|
| 1. pyridoxamine-HCl (Sigma P9380-5G) | 0.5 g |
| 2. Nicotinic acid (Sigma N0765-100G) | 0.1 g |
| 3. Riboflavin (Sigma R4500-5G) | 0.1 g |
| 4. Calcium panthotenate (Sigma P6045-100G) | 0.1 g |
| 5. Thiamin-HCl (Sigma T4625-25G) | 0.1 g |
| 6. Pyridoxine-HCl (Sigma P9755-5G) | 0.2 g |
| 7. 4-aminobenzoic acid sodium salt (Sigma A6928-100G) | 1 g |
| 8. biotin (Sigma B4501-1G) | 1 g |
| 9. folic acid (Sigma F7876-1G) | 0.1 g |
| 10. Vitamin B12 (Sigma V2876-1G) | 0.1 g |
| 11. Orotic acid (Sigma O1756-10G) | 0.5 g |
| 12. Thymidine (Sigma T1895-5G) | 0.5 g |
| 13. Inosine (Sigma I4125-5G) | 0.5 g |
| 14. Lipoic acid (Sigma T5625-5G) | 0.25 g |

Add 700 mL MilliQ water bring the pH up to 10 with NaOH 10 M to dissolve all the vitamins bring pH back to 6.6 with HCl 32% bring the volume of the solution to 1 L with milliQ water

Make 11 mL-aliquots in 50 mL-falcon tubes. Wrap the tubes in aluminium foil. The concentrated vitamin mix can be kept at −20° C. for several months.

Metal solution 100× (volume: 1 L)

| | |
|---|---|
| 1. $MgCl_2 \cdot (H_2O)_6$ (Sigma M2670-100G) | 20 g |
| 2. $CaCl_2 \cdot (H_2O)_2$: (Sigma C2536-500G) | 5 g |
| 3. $Fe(II)Cl_2 \cdot (H_2O)_4$: (Fluka 44936-50G) | 0.5 g |
| 4. $ZnSO_4 \cdot (H_2O)_7$: (Sigma Z1001-500G) | 0.5 g |
| 5. $Cu(II)SO_4 \cdot (H_2O)_5$: (Sigma C3036-250G) | 0.01 g |
| 6. $Co(II)Cl_2 \cdot (H_2O)_6$: (Sigma C2911-100G) | 0.25 g |
| 7. $Mn(II)SO_4 \cdot H_2O$: (Sigma M1144-100G) | 2.8 g |

Add 800 mL milliQ water and 4.8 mL HCl 32% dissolve all metals by stirring bring the volume up to 1 L with milliQ water

Make 40 mL-aliquots in 50 mL-falcon tubes. The concentrated metal mix can be kept at −20° C. for several months DNA precursor mix 50× (volume: 20 mL) Prepare fresh solution every time

| | |
|---|---|
| 1. Adenine (Sigma A2786-5G) | 0.01 g |
| 2. Guanine (Sigma G6779-5G) | 0.01 g |
| 3. Xanthine (Sigma X4002-5G) | 0.01 g |
| 4. Uracil (Sigma U1128-25G) | 0.01 g |

Add 20 mL of filter-sterilized NaOH 0.1 M (the NaOH solution is prepared using milliQ water). Dissolve all DNA precursors by heating the solution (max. temperature: 40° C.).

Amino acid solution 10× (volume: 1 L)

| | |
|---|---|
| 1 L-arginine-HCl (Sigma A5006-100G) | 3.5 g |
| 2 L-cysteine (Sigma C7352-25G) | 2.5 g |
| 3 L-Histidine (Sigma H8000-25G) | 1.5 g |
| 4 L-proline (Sigma P0380-100G) | 6.75 g |
| 5 L-alanine (Sigma A7627-100G) | 2.4 g |
| 6 L-asparagine (Sigma A0884-100G) | 3.5 g |
| 7 L-aspartic acid (Sigma A9256-100G) | 4.55 g |
| 8 L-glycine (Sigma G7126-100G) | 1.75 g |
| 9 Isoleucine (Sigma I2752-100G) | 2.1 g |
| 10 L-leucine (Sigma L8000-100G) | 4.75 g |
| 11 L-lysine-HCl (Sigma L5626-100G) | 4.4 g |
| 12 L-methionine (Sigma M9625-100G) | 1.25 g |
| 13 L-phenylalanine (Sigma P2126-100G) | 2.75 g |
| 14 L-serine (Sigma S4500-100G) | 2.25 g |
| 15 L-threonine (Sigma T8625-100G) | 1.75 g |
| 16 L-tryptophane (Sigma T0254-25G) | 0.5 g |
| 17 L-valine (Sigma V0500-50G) | 3.25 g |
| 18 Glutamine (Sigma G3126-100G) | 3.9 g |
| 19 Glutamic Acid (Sigma G1251-100G) | 3.98 g |

Add 800 mL of milliQ water bring the pH up to 7-7.2 to dissolve all the amino acids bring the volume up to 1 L with milliQ water make 40 mL-aliquots in 50 mL-falcon tubes. The concentrated amino acid solution can be kept for several months at −20° C.

Annex II: More Detailed Protocols

Day 1: Add 100 μL of a glycerol stock in 10 mL of M17 (BD) lactose 1% (w/v) (M17L medium) and let the cells grow during 16 h at 37° C. (overnight).

Day 2:

Centrifuge Day 1-culture (centrifugation parameters: 5000 g, 9 minutes, 15° C.) and perform two washing steps with one volume (10 mL) of CDM (centrifugation parameters: 5000 g, 9 minutes, 15° C.).

Dilute the culture in 10 mL CDM to obtain an $OD_{600\,nm}$ of 0.05.

A small volume of S. thermophilus cultures (300 μL) is then transferred in white microplate with a transparent bottom (655095; Greiner, Alphen a/d Rijn, The Netherlands) and is grown at 37° C. Luminescence at 595 nm and optical density at 600 nm are recorded with the automatic Synergy HT multi-mode microplate reader. The luciferase activity catalysed by LuxAB requires the presence of nonanal as substrate. In this experimental set-up, nonanal (Acros Organics ref. 204-688-5) is supplied to the cultures by placing 50 µL of a solution containing 1% nonanal diluted in mineral oil in the spaces between the wells of a covered microplate (11). The nonanal present in the solution will become volatile and there will be an equilibrium between the concentration of nonanal present in the air and in the culture samples. The luminescence and absorbance are scanned every 10 minutes during 6 hours.

To perform a competence experiment, 1 µg of donor DNA is added in the 300 µL samples in the beginning of incubation. After 6 hours-incubation, plate 100 µL of the non-diluted culture sample that did not receive donor DNA (negative control) on solid selective medium containing 2% agar, M17, lactose 1% and the appropriate antibiotic depending on the donor DNA used. In case of the sample that received DNA, make different 10-fold dilutions of the sample and plate 100 µL on the same solid selective medium. Check the viability of the cells in the samples by plating 10 µL of serial 10-fold dilutions of the cultures on M17, lactose 1% medium. Transformants are picked following 24 h of incubation at 37° C. in anaerobic conditions (gaspak BBL). The transformation rate is obtained by dividing the number of transformed CFUs obtained on selective medium (the antibiotic used depends on the donor DNA used), by the number of viable cells obtained in absence of antibiotic.

Annex III. Examples of Peptides According to the Invention

ANNEX III

| Examples of peptides according to the invention | | |
|---|---|---|
| MKTLKIFVLFSLLIAILPYFAGCL (SEQ ID NO: 69) | MKTLKIFVLFSLLIPILPYFAGCL (SEQ ID NO: 96) | MKKLKLFTLFSLLITILPYFTGCL (SEQ ID NO: 111) |
| KTLKIFVLFSLLIAILPYFAGCL (SEQ ID NO: 70) | KTLKIFVLFSLLIPILPYFAGCL (SEQ ID NO: 97) | KKLKLFTLFSLLITILPYFTGCL (SEQ ID NO: 112) |
| TLKIFVLFSLLIAILPYFAGCL (SEQ ID NO: 71) | TLKIFVLFSLLIPILPYFAGCL (SEQ ID NO: 98) | KLKLFTLFSLLITILPYFTGCL (SEQ ID NO: 113) |
| LKIFVLFSLLIAILPYFAGCL (SEQ ID NO: 72) | LKIFVLFSLLIPILPYFAGCL (SEQ ID NO: 99) | LKLFTLFSLLITILPYFTGCL (SEQ ID NO: 114) |
| KIFVLFSLLIAILPYFAGCL (SEQ ID NO: 73) | KIFVLFSLLIPILPYFAGCL (SEQ ID NO: 100) | KLFTLFSLLITILPYFTGCL (SEQ ID NO: 115) |
| IFVLFSLLIAILPYFAGCL (SEQ ID NO: 74) | IFVLFSLLIPILPYFAGCL (SEQ ID NO: 101) | LFTLFSLLITILPYFTGCL (SEQ ID NO: 116) |
| FVLFSLLIAILPYFAGCL (SEQ ID NO: 75) | FVLFSLLIPILPYFAGCL (SEQ ID NO: 102) | FTLFSLLITILPYFTGCL (SEQ ID NO: 117) |
| VLFSLLIAILPYFAGCL (SEQ ID NO: 76) | VLFSLLIPILPYFAGCL (SEQ ID NO: 103) | TLFSLLITILPYFTGCL (SEQ ID NO: 118) |
| LFSLLIAILPYFAGCL (SEQ ID NO: 77) | LFSLLIPILPYFAGCL (SEQ ID NO: 104) | LFSLLITILPYFTGCL (SEQ ID NO: 119) |
| FSLLIAILPYFAGCL (SEQ ID NO: 78) | FSLLIPILPYFAGCL (SEQ ID NO: 105) | FSLLITILPYFTGCL (SEQ ID NO: 120) |
| SLLIAILPYFAGCL (SEQ ID NO: 79) | SLLIPILPYFAGCL (SEQ ID NO: 106) | SLLITILPYFTGCL (SEQ ID NO: 121) |
| LLIAILPYFAGCL (SEQ ID NO: 80) | LLIPILPYFAGCL (SEQ ID NO: 107) | LLITILPYFTGCL (SEQ ID NO: 122) |
| LIAILPYFAGCL (SEQ ID NO: 81) | LIPILPYFAGCL (SEQ ID NO: 108) | LITILPYFTGCL (SEQ ID NO: 123) |
| IAILPYFAGCL (SEQ ID NO: 82) | IPILPYFAGCL (SEQ ID NO: 109) | ITILPYFTGCL (SEQ ID NO: 124) |
| AILPYFAGCL (SEQ ID NO: 83) | PILPYFAGCL (SEQ ID NO: 110) | TILPYFTGCL (SEQ ID NO: 125) |
| ILPYFAGCL (SEQ ID NO: 84) | | ILPYFTGCL (SEQ ID NO: 126) |
| LPYFAGCL (SEQ ID NO: 85) | | LPYFTGCL (SEQ ID NO: 127) |
| PYFAGCL (SEQ ID NO: 86) | | PYFTGCL (SEQ ID NO: 128) |
| YFAGCL (SEQ ID NO: 87) | | YFTGCL (SEQ ID NO: 129) |

ANNEX III-continued

Examples of peptides according to the invention

| | |
|---|---|
| FAGCL (SEQ ID NO: 88) | FTGCL (SEQ ID NO: 130) |
| AGCL (SEQ ID NO: 89) | TGCL (SEQ ID NO: 131) |

REFERENCES

Throughout this application, various references describe the state of the art to which this invention pertains. The disclosures of these references are hereby incorporated by reference into the present disclosure.

1. Hols, P., F. Hancy, L. Fontaine, B. Grossiord, D. Prozzi, N. Leblond-Bourget, B. Decaris, A. Bolotin, C. Delorme, E. S. Dusko, E. Guedon, V. Monnet, P. Renault, and M. Kleerebezem. 2005. New insights in the molecular biology and physiology of Streptococcus thermophilus revealed by comparative genomics. FEMS Microbiol. Rev. 29:435-463.
2. Martin, B., Y. Quentin, G. Fichant, and J. P. Clayerys. 2006. Independent evolution of competence regulatory cascades in streptococci? Trends Microbiol. 14:339-345.
3. Clayerys, J. P. and B. Martin. 2003. Bacterial "competence" genes: signatures of active transformation, or only remnants? Trends Microbiol. 11:161-165.
4. Clayerys, J. P., M. Prudhomme, and B. Martin. 2006. Induction of competence regulons as a general response to stress in gram-positive bacteria. Annu. Rev. Microbiol. 60:451-475.
5. Blomqvist, T., H. Steinmoen, and L. S. Havarstein. 2006. Natural genetic transformation: A novel tool for efficient genetic engineering of the dairy bacterium Streptococcus thermophilus. Appl. Environ. Microbiol. 72:6751-6756.
6. L. Fontaine, C. Boutry, E. Guedon, A. Guillot, M. Ibrahim, B. Grossiord and P. Hols 2007. Quorum sensing regulation of the production of Bpi bacteriocins in Streptococcus thermophilus. J. Bacteriol. 189:7195-7205
7. R. Gardan, C. Besset, A. Guillot, C. Gitton, and V. Monnet. 2009. The oligopeptide transport system is essential for the development of natural competence in Streptococcus thermophilus strain LMD-9. J. Bacteriol. DOI:10.1128/JB.00257-09
8. L. Slamti and D. Lereclus. 2002. A cell-cell signaling peptide activates the P1cR virulence regulon in bacteria of the Bacillus cereus group. EMBO J. 21:4550-4559.
9. B. K. Kozlowicz B K, K. Shi, Z. Y. Gu, D. H. Ohlendorf, C. A. Earhart, G. M. Dunny. 2006. Molecular basis for control of conjugation by bacterial pheromone and inhibitor peptides. Mol. Microbiol. 62:958-869.
10. M. Ibrahim, P. Nicolas, P. Bessières, A. Bolotin, V. Monnet and R. Gardan. 2007. Control of the transcription of a short gene encoding a cyclic peptide in Streptococcus thermophilus: a new quorum-sensing system? J. Bacteriol. 189:8844-8854.
11. H. Bachmann, M. Kleerebezem, J. E. van Hylckama Vlieg. 2008. High-throughput identification and validation of in situ-expressed genes of Lactococcus lactis. Appl. Environ. Microbiol. 74:4727-4736.
12. Eddy S.R., 2004. Where did the BLOSUM62 alignment score matrix come from? Nature Biotechnology 22, 1035-1036.
13. Fernandez-Espla, M.D., P. Garault, V. Monnet and F. Rul. 2000. Streptococcus thermophilus cell wall-anchored proteinase: release, purification, and biochemical and genetic characterization. Appl. Environ. Microbiol. 66:4772-4778.
14. Huggins A. R. and W. E. Sandine. 1984. Differentiation of fast and slow milk-coagulating isolates in strains of lactic Streptococci. J. Dairy Sci. 67:1674-1679.
15. Makarova et al. 2006. Comparative genomics of the lactic acid bacteria. Proc Natl Acad Sci USA. 103:15611-15616.
16. Bolotin et al. 2004. Complete sequence and comparative genome analysis of the dairy bacterium Streptococcus thermophilus. Nat. Biotechnol. 22:1554-1558
17. Spinnler H. E, and G. Corrieu. 1989. Automatic method to quantify starter activity based on pH measurement. J. Dairy Res. 56:755-764
18. Lambert, J. M., Bongers, R. S., and M. Kleerebezem. 2007. Cre-lox-based system for multiple gene deletions and selectable-marker removal in Lactobacillus plantarum. Appl. Environ. Microbiol. 73:1126-35.

The invention claimed is:

1. An isolated peptide comprising at least 7 amino acids and at most 24 acids, wherein the isolated peptide has an amino acid sequence as set forth in SEQ ID NO: 1 when the isolated peptide is 24 amino acids long and the isolated peptide comprises a portion of SEQ ID NO: 1 including at least PYFAGCL SEQ ID NO: 86, when the isolated peptide includes 23 amino acids or less, and wherein said peptide induces and increases competence in a S. thermophilus strain.

2. The isolated peptide according to claim 1, wherein the isolated peptide induces and increases competence in the S. thermophilus strain LMD-9 in which the gene encoding SEQ ID NO:1 has been inactivated.

3. The isolated peptide according to claim 1, wherein said isolated peptide includes at most 23 amino acids.

4. The isolated peptide according to claim 1, wherein the C-terminal end of said isolated peptide has an amino acid sequence of AGCL SEQ ID NO: 89.

5. The isolated peptide according to claim 1, wherein the C-terminal end of said isolated peptide has an amino acid sequence selected from the group consisting of: PYFAGCL SEQ ID NO: 86, LPYFAGCL SEQ ID NO: 85, or ILPYFAGCL SEQ ID NO: 84.

6. The isolated peptide according to claim 1, wherein said isolated peptide is selected from the group consisting of: KTLKIFVLFSLLIAILPYFAGCL SEQ ID NO: 70, TLKIFVLFSLLIAILPYFAGCL SEQ ID NO: 71, LKIFVLFSLLIAILPYFAGCL SEQ ID NO: 72, KIFVLFSLLIAILPYFAGCL SEQ ID NO: 73, IFVLFSLLIAILPYFAGCL SEQ ID NO: 74, FVLFSLLIAILPYFAGCL SEQ ID NO: 75, VLFSLLIAILPYFAGCL SEQ ID NO: 76, LFSLLIAILPYFAGCL SEQ ID NO: 77, FSLLIAILPYFAGCL SEQ ID NO: 78, SLLIAILPYFAGCL SEQ ID NO: 79, LLIAILPYFAGCL SEQ ID NO: 80, LIAILPYFAGCL SEQ ID NO: 81, and IAILPYFAGCL SEQ ID NO: 82.

7. The isolated peptide according to claim 1, wherein said isolated peptide comprises the amino acid sequence LPYFAGCL SEQ ID NO: 85, ILPYFAGCL SEQ ID NO: 84, or AILPYFAGCL SEQ ID NO: 83.

8. The isolated peptide according to claim 1, wherein the C-terminal end of said isolated peptide has an amino acid sequence of AILPYFAGCL SEQ ID NO: 83.

9. The isolated peptide according to claim 1, wherein the isolated peptide is synthetic.

10. An isolated peptide comprising at least 7 amino acids and at most 19 acids, wherein the isolated peptide has an amino acid sequence as set forth in SEQ ID NO: 4 when the isolated peptide is 24 amino acids long and the isolated peptide comprises a portion of SEQ ID NO: 4 including at least PYFAGCL SEQ ID NO: 86, when the isolated peptide includes 19 amino acids or less, and wherein said peptide induces or increases competence in a S. thermophilus strain.

11. The isolated peptide according to claim 10, wherein said isolated peptide includes at most 18.

12. The isolated peptide according to claim 1, wherein said isolated peptide contains at most 23 amino acids.

13. The isolated peptide according to claim 1, wherein said isolated peptide contains at most 22 amino acids.

14. The isolated peptide according to claim 1, wherein said isolated peptide contains at most 21 amino acids.

15. The isolated peptide according to claim 1, wherein said isolated peptide contains at most 20 amino acids.

16. The isolated peptide according to claim 1, wherein said isolated peptide contains at most 19 amino acids.

17. The isolated peptide according to claim 1, wherein said isolated peptide contains at most 18 amino acids.

18. The isolated peptide according to claim 1, wherein said isolated peptide contains at most 17 amino acids.

19. The isolated peptide according to claim 1, wherein said isolated peptide contains at most 16 amino acids.

20. The isolated peptide according to claim 1, wherein said isolated peptide contains at most 15 amino acids.

21. The isolated peptide according to claim 1, wherein said isolated peptide contains at most 14 amino acids.

22. The isolated peptide according to claim 1, wherein said isolated peptide contains at most 13 amino acids.

23. The isolated peptide according to claim 1, wherein said isolated peptide contains at most 12 amino acids.

24. The isolated peptide according to claim 1, wherein said isolated peptide contains at most 11 amino acids.

25. The isolated peptide according to claim 1, wherein said isolated peptide contains at most 10 amino acids.

26. The isolated peptide according to claim 1, wherein said isolated peptide contains at most 9 amino acids.

27. The isolated peptide according to claim 1, wherein said isolated peptide contains at most 8 amino acids.

28. The isolated peptide according to claim 1, wherein said isolated peptide consists of 7 amino acids.

29. The isolated peptide according to claim 10, wherein said isolated peptide consists of 17 amino acids.

30. The isolated peptide according to claim 10, wherein said isolated peptide consists of 16 amino acids.

31. The isolated peptide according to claim 10, wherein said isolated peptide consists of 15 amino acids.

32. The isolated peptide according to claim 10, wherein said isolated peptide consists of 14 amino acids.

33. The isolated peptide according to claim 10, wherein said isolated peptide consists of 13 amino acids.

34. The isolated peptide according to claim 10, wherein said isolated peptide consists of 12 amino acids.

35. The isolated peptide according to claim 10, wherein said isolated peptide consists of 11 amino acids.

36. The isolated peptide according to claim 10, wherein said isolated peptide consists of 10 amino acids.

37. The isolated peptide according to claim 10, wherein said isolated peptide consists of 9 amino acids.

38. The isolated peptide according to claim 10, wherein said isolated peptide consists of 8 amino acids.

39. The isolated peptide according to claim 10, wherein said isolated peptide consists of 7 amino acids.

40. A kit-of-parts comprising:
a bacterium belonging to the Streptococcus genus in a first part; and
in a second part, the peptide according to claim 1.

41. A method for inducing and/or increasing competence in a bacterium belonging to the *Streptococcus* genus, wherein said bacterium is incubated in a medium comprising a peptide according to claim 1.

* * * * *

SEQUENCE LISTING

<160> NUMBER OF SEQ ID NOS: 131

<210> SEQ ID NO 1
<211> LENGTH: 24
<212> TYPE: PRT
<213> ORGANISM: Streptococcus thermophilus

<400> SEQUENCE: 1

Met Lys Thr Leu Lys Ile Phe Val Leu Phe Ser Leu Leu Ile Ala Ile
1               5                   10                  15

Leu Pro Tyr Phe Ala Gly Cys Leu
            20

<210> SEQ ID NO 2

-continued

```
<211> LENGTH: 24
<212> TYPE: PRT
<213> ORGANISM: Streptococcus thermophilus

<400> SEQUENCE: 2

Met Lys Thr Leu Lys Ile Phe Val Leu Phe Ser Leu Leu Ile Pro Ile
1               5                   10                  15

Leu Pro Tyr Phe Ala Gly Cys Leu
            20

<210> SEQ ID NO 3
<211> LENGTH: 24
<212> TYPE: PRT
<213> ORGANISM: Streptococcus salivarius

<400> SEQUENCE: 3

Met Lys Lys Leu Lys Leu Phe Thr Leu Phe Ser Leu Leu Ile Thr Ile
1               5                   10                  15

Leu Pro Tyr Phe Thr Gly Cys Leu
            20

<210> SEQ ID NO 4
<211> LENGTH: 19
<212> TYPE: PRT
<213> ORGANISM: Streptococcus thermophilus

<400> SEQUENCE: 4

Ile Phe Val Leu Phe Ser Leu Leu Ile Ala Ile Leu Pro Tyr Phe Ala
1               5                   10                  15

Gly Cys Leu

<210> SEQ ID NO 5
<211> LENGTH: 17
<212> TYPE: PRT
<213> ORGANISM: Streptococcus thermophilus

<400> SEQUENCE: 5

Ile Phe Val Leu Phe Ser Leu Leu Ile Ala Ile Leu Pro Tyr Phe Ala
1               5                   10                  15

Gly

<210> SEQ ID NO 6
<211> LENGTH: 75
<212> TYPE: DNA
<213> ORGANISM: Streptococcus thermophilus

<400> SEQUENCE: 6
ttgaaaaccc tgaaaatatt tgtactattt tcactactta ttgctatctt gccttatttt    60
gcaggatgtc tttaa                                                     75

<210> SEQ ID NO 7
<211> LENGTH: 75
<212> TYPE: DNA
<213> ORGANISM: Streptococcus thermophilus

<400> SEQUENCE: 7
ttgaaaaccc tgaaaatatt tgtactattt tcactactta ttcctatctt gccttatttt    60
gcaggatgtc tttaa                                                     75

<210> SEQ ID NO 8
<211> LENGTH: 75
<212> TYPE: DNA
```

<213> ORGANISM: Streptococcus salivarius

<400> SEQUENCE: 8
ttgaaaaaac taaaattatt tacactattc tcactactta tcactatctt gccctatttt    60
acaggttgtc tttaa    75

<210> SEQ ID NO 9
<211> LENGTH: 299
<212> TYPE: PRT
<213> ORGANISM: Streptococcus thermophilus

<400> SEQUENCE: 9

```
Met Asn Leu Lys Asp Ser Ile Gly Leu Arg Ile Lys Thr Glu Arg Glu
1               5                   10                  15

Arg Gln Gln Met Ser Arg Glu Val Leu Cys Leu Asp Gly Ala Glu Leu
            20                  25                  30

Thr Val Arg Gln Leu Ile Arg Ile Glu Lys Gly Glu Ser Leu Pro Ser
        35                  40                  45

Leu Asp Arg Leu Ser Tyr Ile Ala Lys Arg Leu Gly Lys Ser Met Thr
    50                  55                  60

Glu Leu Leu Asp Gln Asp Asn Ile Thr Ile Pro Asp Glu Tyr Tyr Glu
65                  70                  75                  80

Met Lys Asn Arg Leu Ile Lys Phe Pro Thr Tyr Arg Asn Pro Asp Arg
                85                  90                  95

Ile Lys Ser Lys Leu Thr Leu Ile Glu Glu Val Tyr Glu Lys Phe Phe
            100                 105                 110

Asp Ile Leu Pro Glu Glu Leu Leu Thr Leu Asp Ile Leu Glu Asn
        115                 120                 125

Ile Leu Ser Phe Thr Ser Trp Glu Glu Ser Pro Lys Val Glu Glu Ile
    130                 135                 140

Tyr Glu Asp Leu Phe Glu Gln Val Lys Arg Lys Arg Lys Phe Ser Thr
145                 150                 155                 160

Asn Asp Leu Leu Val Ile Asp Tyr Tyr Phe Phe His Leu Tyr Gly Arg
                165                 170                 175

Lys Gln Tyr Asp Lys Lys Leu Phe Glu Arg Ile Ile Lys Arg Val Leu
            180                 185                 190

Asn Gln Glu Ile Trp Thr Asp Asp Val Tyr Asn Ile Val Leu Phe Asn
        195                 200                 205

Asp Leu Met Ala Ile Ala Ala Leu Lys Ile Phe His Asn Ser Phe Ser
    210                 215                 220

Asp Phe Leu Thr Val Val Asp Lys Ala Leu Ala Val Ile Glu Lys Ser
225                 230                 235                 240

Gln Leu Tyr Ser Tyr Lys Pro Ser Val Phe Val Leu Lys Ala Lys Tyr
                245                 250                 255

Glu Leu Leu His Lys Glu Asn Lys Lys Glu Ala Ala Glu Asn Tyr Asp
            260                 265                 270

Lys Ala Ile Val Phe Ala Ser Val Leu Glu Asp Ser Val Leu Glu Glu
        275                 280                 285

Ser Ile Lys Ala Gly Lys Leu Ala Asp Gly Leu
    290                 295
```

<210> SEQ ID NO 10
<211> LENGTH: 299
<212> TYPE: PRT
<213> ORGANISM: Streptococcus thermophilus

<400> SEQUENCE: 10

Met Asn Ile Lys Asp Ser Ile Gly Leu Arg Ile Lys Thr Glu Arg Glu
1               5                   10                  15

Arg Gln Gln Met Ser Arg Glu Val Leu Cys Leu Asp Gly Ala Glu Leu
            20                  25                  30

Thr Val Arg Gln Leu Ile Arg Ile Glu Lys Gly Glu Ser Leu Pro Ser
        35                  40                  45

Leu Asp Arg Leu Ser Tyr Ile Ala Lys Arg Leu Gly Lys Ser Met Thr
50                  55                  60

Glu Leu Leu Asp Gln Asp Asn Ile Thr Ile Pro Asp Glu Tyr Tyr Glu
65                  70                  75                  80

Met Lys Asn Arg Leu Ile Lys Phe Pro Thr Tyr Arg Asn Pro Asp Arg
                85                  90                  95

Ile Lys Ser Lys Leu Thr Leu Ile Glu Glu Val Tyr Glu Lys Phe Phe
            100                 105                 110

Asp Ile Leu Pro Glu Glu Leu Leu Thr Leu Asp Ile Leu Glu Asn
            115                 120                 125

Ile Leu Ser Phe Thr Ser Trp Glu Glu Ser Pro Lys Val Glu Glu Ile
        130                 135                 140

Tyr Glu Asp Leu Phe Glu Gln Val Lys Arg Lys Arg Lys Phe Ser Thr
145                 150                 155                 160

Asn Asp Leu Leu Val Ile Asp Tyr Tyr Phe Phe His Leu Tyr Gly Arg
                165                 170                 175

Lys Gln Tyr Asp Lys Lys Leu Phe Glu Arg Ile Ile Lys Arg Val Leu
            180                 185                 190

Asn Gln Glu Ile Trp Thr Asp Val Tyr Asn Ile Val Leu Phe Asn
        195                 200                 205

Asp Leu Met Ala Ile Ala Ala Leu Lys Ile Phe His Asn Ser Phe Ser
210                 215                 220

Asp Phe Leu Thr Val Val Asp Lys Ala Leu Ala Val Ile Glu Asn Ser
225                 230                 235                 240

Gln Leu Tyr Ser Tyr Lys Pro Ser Val Phe Val Leu Lys Ala Lys Tyr
                245                 250                 255

Glu Leu Leu His Lys Glu Asn Lys Lys Glu Ala Ala Glu Asn Tyr Asp
            260                 265                 270

Lys Ala Ile Met Phe Ala Ser Val Leu Glu Asp Ser Val Leu Glu Glu
            275                 280                 285

Ser Ile Lys Ala Gly Lys Leu Ala Asp Gly Leu
        290                 295

<210> SEQ ID NO 11
<211> LENGTH: 299
<212> TYPE: PRT
<213> ORGANISM: Streptococcus salivarius

<400> SEQUENCE: 11

Met Asn Ile Lys Asp Ser Ile Gly Leu Arg Ile Lys Thr Glu Arg Glu
1               5                   10                  15

Leu Gln Gln Met Ser Arg Glu Val Leu Cys Leu Asp Gly Ala Glu Leu
            20                  25                  30

Thr Val Arg Gln Leu Ile Arg Ile Glu Lys Gly Glu Ser Leu Pro Ser
        35                  40                  45

Leu Asp Lys Leu Ser Tyr Ile Ala Lys Arg Leu Gly Lys Ser Met Thr
50                  55                  60

Asp Leu Leu Asp His Asp Asn Ile Thr Ile Pro Asp Glu Tyr Tyr Glu
65                  70                  75                  80

```
Met Lys Asn Arg Leu Ile Lys Phe Pro Thr Tyr Arg Asn Pro Glu Arg
                85                  90                  95

Ile Lys Ala Lys Leu Ala Leu Ile Glu Glu Val Tyr Glu Lys Phe Phe
            100                 105                 110

Glu Leu Leu Ser Glu Glu Leu Thr Leu Asp Ile Leu Glu Asn
            115                 120                 125

Ile Leu Ser Phe Thr Ser Trp Glu Ser Pro Lys Val Glu Glu Ile
        130                 135                 140

Tyr Glu Asp Leu Phe Glu Gln Val Lys Arg Lys Lys Phe Ser Thr
145                 150                 155                 160

Asn Asp Leu Leu Val Ile Asp Tyr Tyr Phe Phe His Leu Tyr Gly Arg
                165                 170                 175

Lys Gln Tyr Asp Lys Lys Leu Phe Glu Arg Ile Val Lys Arg Val Leu
            180                 185                 190

Asn Gln Glu Ile Trp Thr Asp Asp Val Tyr Asn Ile Val Leu Phe Asn
            195                 200                 205

Asp Leu Met Ala Ile Ala Ala Leu Lys Ile Phe His Asn Ser Phe Ser
        210                 215                 220

Asp Phe Leu Thr Val Val Asp Lys Ala Leu Ala Val Ile Glu Lys Ser
225                 230                 235                 240

Gln Phe Tyr Ser Tyr Lys Pro Ser Val Phe Val Leu Lys Ala Lys Tyr
                245                 250                 255

Glu Leu Leu His Lys Gly Asn Lys Lys Glu Ala Ala Glu Asn Tyr Asp
            260                 265                 270

Lys Ala Ile Met Phe Ala Ser Val Leu Glu Asp Ser Val Leu Glu Glu
            275                 280                 285

Ser Ile Arg Ala Gly Lys Ala Ala Asp Gly Leu
        290                 295

<210> SEQ ID NO 12
<211> LENGTH: 900
<212> TYPE: DNA
<213> ORGANISM: Streptococcus thermophilus

<400> SEQUENCE: 12
ttgaacttaa aagacagcat tggactaaga atcaaaactg agcgtgaacg ccaacagatg      60
tcacgtgaag tgctatgttt agatggtgcg gaattgactg ttcgccagtt aattcgtatt     120
gaaaaggggg agtctctccc gtctttagat agattatcgt atattgctaa acgtttagga     180
aaaagtatga cagagttatt ggatcaagac aatattacca ttcctgacga atattatgaa     240
atgaagaatc gtttgattaa gtttccaacg tacagaaacc ctgacagaat aaagtctaaa     300
cttactttga ttgaggaagt ctatgagaaa ttttttgata ttcttccaga agaagaatta     360
ttaactttag acattctcga aaatatattg agttttacta gctggggagga gagtccaaaa     420 gttgaggaga tatatgaaga cttgtttgaa caagtcaaaa ggaagaggaa attctcaact     480
aacgatttat tagtcattga ctattatttc tttcatcttt atgggagaaa acagtatgac     540
aaaaaactat ttgaaagaat tataaagaga gtattaaatc aggaaatttg gacagatgat     600
gtttacaata ttgtttttatt taatgatttg atggctattg ctgcttttaaa gattttttcac     660 aattccttct cagacttctt aacagttgtg gataaagcct tagctgtcat agaaaaatca     720
caattatata gctacaagcc tagtgttttt gtacttaagg ctaaatatga acttctgcat     780
aaagaaaaca gaaagagggc tgcagagaat tatgataagg ccatagtgtt tgcttccgtt     840
ttggaagact cggttttaga ggaaagtata aaggcaggaa aattggcaga tggtttatag     900
```

<210> SEQ ID NO 13
<211> LENGTH: 900
<212> TYPE: DNA
<213> ORGANISM: Streptococcus thermophilus

<400> SEQUENCE: 13

```
ttgaacataa aagacagcat tggactaaga atcaaaactg agcgtgaacg ccaacagatg      60
tcacgtgaag tgctatgttt agatggtgcg gaattgactg ttcgccagtt aattcgtatt     120
gaaaaggggg agtctctccc gtctttagat agattatcgt atattgctaa acgtttagga     180
aaaagtatga cagagttatt ggatcaagac aatattacca ttcctgacga atattatgaa     240
atgaagaatc gtttgattaa gtttccaacg tacagaaacc ctgacagaat aaagtctaaa     300
cttactttga ttgaggaagt ctatgagaaa ttttttgata ttcttccaga agaagaatta     360
ttaactctag acattctcga aaatatattg agttttacta gctgggagga gagtccaaaa     420
gttgaggaga tatatgaaga cttgtttgaa caagtcaaaa ggaagaggaa attctcaact     480
aacgatttat tagtcattga ctattatttc tttcatcttt atgggagaaa acagtatgac     540
aaaaaactat ttgaaagaat tataaagaga gtattaaatc aggaaatttg gacagatgat     600
gtttacaata ttgttttatt taatgatttg atggctattg ctgctttaaa gattttttcac     660
aattccttct cagacttctt aacagttgtg ataaagcct  tagctgtcat agaaaactca     720
caattatata gctacaagcc tagtgttttt gtacttaagg ctaaatatga acttctgcat     780
aaagaaaaca gaaagaggc tgcagagaat tatgataagg ccataatgtt tgcttccgtt     840
ttggaagact cggttttaga ggaaagtata aaggcaggaa aattggcaga tggtttatag     900
```

<210> SEQ ID NO 14
<211> LENGTH: 900
<212> TYPE: DNA
<213> ORGANISM: Streptococcus salivarius

<400> SEQUENCE: 14

```
ttgaacataa aagacagcat tggactaaga atcaaaactg agcgtgaact ccagcagatg      60
tcacgtgaag tactatgttt agatggtgcg gaattaactg ttcgtcagtt aattcgtatt     120
gaaaagggag aatctctccc gtctttggat aaattatctt atatcgccaa acgtttagga     180
aaaagtatga ctgatttatt ggatcatgac aatattacta tccctgacga atactacgag     240
atgaagaatc gtttgattaa gtttccaacg tatagaaatc cagaaagaat aaaggctaaa     300
cttgccttaa ttgaggaggt ctacgagaaa ttctttgaac ttctctcaga agaagaattg     360
ttaactctag atattttgga aaatattttg agttttacta gttgggaaga gagtccaaaa     420
gttgaggaga tatatgaaga cttgtttgaa caagtcaaaa ggaagaagaa attctcaact     480
aacgatttat tagttattga ctattatttc ttccatcttt atggaagaaa acagtatgat     540
aaaaaacttt tgaaagaat cgtaaagaga gtattaaatc aggaaatttg gacagacgat     600
gtttataata ttgttttatt taatgatttg atggctatcg ctgctttgaa gattttttcat     660
aattccttct cagacttctt aacagttgtg ataaagcct  tagctgttat agaaaaatca     720
caattctata gctataaacc tagtgttttt gttctcaaag ccaaatatga acttcttcat     780
aaaggaaaca gaaagaggc tgcagaaaat tatgataagg ccataatgtt tgcttccgtt     840
ttagaagact cggttttaga ggaaagtata agggcaggaa aagcggcaga tggtttatag     900
```

<210> SEQ ID NO 15
<211> LENGTH: 31

```
<212> TYPE: DNA
<213> ORGANISM: Artificial
<220> FEATURE:
<223> OTHER INFORMATION: primer

<400> SEQUENCE: 15
aaacaatggt ggcccaggat caatgattgg g                            31

<210> SEQ ID NO 16
<211> LENGTH: 41
<212> TYPE: DNA
<213> ORGANISM: Artificial
<220> FEATURE:
<223> OTHER INFORMATION: primer

<400> SEQUENCE: 16
ccttatggga tttatcttcc ttagattctt agtccaatgc t                 41

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
taaggaagat aaatcccata agg                                     23

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
ttcacgttac taaagggaat gta                                     23

<210> SEQ ID NO 19
<211> LENGTH: 39
<212> TYPE: DNA
<213> ORGANISM: Artificial
<220> FEATURE:
<223> OTHER INFORMATION: primer

<400> SEQUENCE: 19
tacattccct ttagtaacgt gaagttttgg aagactcgg                    39

<210> SEQ ID NO 20
<211> LENGTH: 35
<212> TYPE: DNA
<213> ORGANISM: Artificial
<220> FEATURE:
<223> OTHER INFORMATION: primer

<400> SEQUENCE: 20
caataatagc agtattgacc tgactatttg cctcc                        35

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
taagagtgct attggtgttc tcttgc                                  26
```

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
tcatggaatt tcacctcaat ttcttgc                                27

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
ggtattgatc ccgaattcag atgtttgtag                             30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
ggctggatgg cataaccgag cttttgtttc                             30

<210> SEQ ID NO 25
<211> LENGTH: 39
<212> TYPE: DNA
<213> ORGANISM: Artificial
<220> FEATURE:
<223> OTHER INFORMATION: primer

<400> SEQUENCE: 25
ttgcttaatg ctgtctatcc aacttatgac cgtattcgc                   39

<210> SEQ ID NO 26
<211> LENGTH: 44
<212> TYPE: DNA
<213> ORGANISM: Artificial
<220> FEATURE:
<223> OTHER INFORMATION: primer

<400> SEQUENCE: 26
ccttatggga tttatcttcc ttacaaaata taactccttt taac             44

<210> SEQ ID NO 27
<211> LENGTH: 23
<212> TYPE: DNA
<213> ORGANISM: Artificial
<220> FEATURE:
<223> OTHER INFORMATION: primer

<400> SEQUENCE: 27
taaggaagat aaatcccata agg                                    23

<210> SEQ ID NO 28
<211> LENGTH: 23
<212> TYPE: DNA
<213> ORGANISM: Artificial
<220> FEATURE:
<223> OTHER INFORMATION: primer

```
<400> SEQUENCE: 28
ttcacgttac taaagggaat gta                                    23

<210> SEQ ID NO 29
<211> LENGTH: 41
<212> TYPE: DNA
<213> ORGANISM: Artificial
<220> FEATURE:
<223> OTHER INFORMATION: primer

<400> SEQUENCE: 29
tacattccct ttagtaacgt gaataataag gagccatcat g                41

<210> SEQ ID NO 30
<211> LENGTH: 40
<212> TYPE: DNA
<213> ORGANISM: Artificial
<220> FEATURE:
<223> OTHER INFORMATION: primer

<400> SEQUENCE: 30
aaacttcttg aagacaatta ttggctacct tggcttgctg                  40

<210> SEQ ID NO 31
<211> LENGTH: 28
<212> TYPE: DNA
<213> ORGANISM: Artificial
<220> FEATURE:
<223> OTHER INFORMATION: primer

<400> SEQUENCE: 31
ttgttggact ttcgcgtatt tatgtagg                               28

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
ttgagttgac cttttcttc cttattcac                               29

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
agctctagat aaataatagt taaaaggag                              29

<210> SEQ ID NO 34
<211> LENGTH: 32
<212> TYPE: DNA
<213> ORGANISM: Artificial
<220> FEATURE:
<223> OTHER INFORMATION: primer

<400> SEQUENCE: 34
tttctgcagt tacattttgg catgatggct cc                          32

<210> SEQ ID NO 35
<211> LENGTH: 28
```

```
<212> TYPE: DNA
<213> ORGANISM: Artificial
<220> FEATURE:
<223> OTHER INFORMATION: primer

<400> SEQUENCE: 35
aatctttgat cgtttctacc gagtagac                                    28

<210> SEQ ID NO 36
<211> LENGTH: 26
<212> TYPE: DNA
<213> ORGANISM: Artificial
<220> FEATURE:
<223> OTHER INFORMATION: primer

<400> SEQUENCE: 36
taactaatcg aaaactccag taggag                                      26

<210> SEQ ID NO 37
<211> LENGTH: 33
<212> TYPE: DNA
<213> ORGANISM: Artificial
<220> FEATURE:
<223> OTHER INFORMATION: primer

<400> SEQUENCE: 37
aaagagctca ataaatgaag gagaaaaact agg                              33

<210> SEQ ID NO 38
<211> LENGTH: 33
<212> TYPE: DNA
<213> ORGANISM: Artificial
<220> FEATURE:
<223> OTHER INFORMATION: primer

<400> SEQUENCE: 38
aaagtcgaca acttgtgata aagctagtgt tgg                              33

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
ttatgtcttg gcccttgtca aggatttggg                                  30

<210> SEQ ID NO 40
<211> LENGTH: 44
<212> TYPE: DNA
<213> ORGANISM: Artificial
<220> FEATURE:
<223> OTHER INFORMATION: primer

<400> SEQUENCE: 40
ccttatggga tttatcttcc ttattcaatc tttcgtaatc cttt                  44

<210> SEQ ID NO 41
<211> LENGTH: 41
<212> TYPE: DNA
<213> ORGANISM: Artificial
<220> FEATURE:
<223> OTHER INFORMATION: primer

<400> SEQUENCE: 41
tacattccct ttagtaacgt gaaaaagcaa tgttcatgac c                     41
```

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
tttactagtc ccagatgcac gcatacgacg                                    30

<210> SEQ ID NO 43
<211> LENGTH: 23
<212> TYPE: DNA
<213> ORGANISM: Artificial
<220> FEATURE:
<223> OTHER INFORMATION: primer

<400> SEQUENCE: 43
taaggaagat aaatcccata agg                                           23

<210> SEQ ID NO 44
<211> LENGTH: 23
<212> TYPE: DNA
<213> ORGANISM: Artificial
<220> FEATURE:
<223> OTHER INFORMATION: primer

<400> SEQUENCE: 44
tacattccct ttagtaacgt gaa                                           23

<210> SEQ ID NO 45
<211> LENGTH: 30
<212> TYPE: DNA
<213> ORGANISM: Artificial
<220> FEATURE:
<223> OTHER INFORMATION: primer

<400> SEQUENCE: 45
ttgatgatga ggtggctgat atggacaagg                                    30

<210> SEQ ID NO 46
<211> LENGTH: 27
<212> TYPE: DNA
<213> ORGANISM: Artificial
<220> FEATURE:
<223> OTHER INFORMATION: primer

<400> SEQUENCE: 46 ttagacccctt tacgacgctt gccttgg                                      27

<210> SEQ ID NO 47
<211> LENGTH: 33
<212> TYPE: DNA
<213> ORGANISM: Artificial
<220> FEATURE:
<223> OTHER INFORMATION: primer

<400> SEQUENCE: 47
taagttggag tatgctgttg gtcgtgtgga cgc                                33

<210> SEQ ID NO 48
<211> LENGTH: 33
<212> TYPE: DNA
<213> ORGANISM: Artificial
<220> FEATURE:
<223> OTHER INFORMATION: primer

```
<400> SEQUENCE: 48
ttatctttag ccttgaccaa ttcttgtgag gcc                          33

<210> SEQ ID NO 49
<211> LENGTH: 26
<212> TYPE: DNA
<213> ORGANISM: Artificial
<220> FEATURE:
<223> OTHER INFORMATION: primer

<400> SEQUENCE: 49
tttatgcgtg agaatgttac agtcta                                  26

<210> SEQ ID NO 50
<211> LENGTH: 26
<212> TYPE: DNA
<213> ORGANISM: Artificial
<220> FEATURE:
<223> OTHER INFORMATION: primer

<400> SEQUENCE: 50
tgtaaatttg gaaagttaca cgttac                                  26

<210> SEQ ID NO 51
<211> LENGTH: 30
<212> TYPE: DNA
<213> ORGANISM: Artificial
<220> FEATURE:
<223> OTHER INFORMATION: primer

<400> SEQUENCE: 51
ttatgtcttg gcccttgtca aggatttggg                              30

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
tttactagtc ccagatgcac gcatacgacg                              30

<210> SEQ ID NO 53
<211> LENGTH: 33
<212> TYPE: DNA
<213> ORGANISM: Artificial
<220> FEATURE:
<223> OTHER INFORMATION: primer

<400> SEQUENCE: 53
taagttggag tatgctgttg gtcgtgtgga cgc                          33

<210> SEQ ID NO 54
<211> LENGTH: 44
<212> TYPE: DNA
<213> ORGANISM: Artificial
<220> FEATURE:
<223> OTHER INFORMATION: primer

<400> SEQUENCE: 54
ccttatggga tttatcttcc ttattcaatc tttcgtaatc cttt              44

<210> SEQ ID NO 55
<211> LENGTH: 33
```

<210> SEQ ID NO 55
<211> LENGTH: 33
<212> TYPE: DNA
<213> ORGANISM: Artificial
<220> FEATURE:
<223> OTHER INFORMATION: primer

<400> SEQUENCE: 55
ttatctttag ccttgaccaa ttcttgtgag gcc                              33

<210> SEQ ID NO 56
<211> LENGTH: 41
<212> TYPE: DNA
<213> ORGANISM: Artificial
<220> FEATURE:
<223> OTHER INFORMATION: primer

<400> SEQUENCE: 56
tacattccct ttagtaacgt gaaaaagcaa tgttcatgac c                     41

<210> SEQ ID NO 57
<211> LENGTH: 28
<212> TYPE: DNA
<213> ORGANISM: Artificial
<220> FEATURE:
<223> OTHER INFORMATION: primer

<400> SEQUENCE: 57
ctaccgagtt aacagcggtt ggttgggc                                    28

<210> SEQ ID NO 58
<211> LENGTH: 27
<212> TYPE: DNA
<213> ORGANISM: Artificial
<220> FEATURE:
<223> OTHER INFORMATION: primer

<400> SEQUENCE: 58
ttggtcctca aaccagcct ccaactg                                      27

<210> SEQ ID NO 59
<211> LENGTH: 24
<212> TYPE: DNA
<213> ORGANISM: Artificial
<220> FEATURE:
<223> OTHER INFORMATION: primer

<400> SEQUENCE: 59
tagtttctca gagatagact ttgg                                        24

<210> SEQ ID NO 60
<211> LENGTH: 27
<212> TYPE: DNA
<213> ORGANISM: Artificial
<220> FEATURE:
<223> OTHER INFORMATION: primer

<400> SEQUENCE: 60
tttacctcgt ccagtcactt tgcaagc                                     27

<210> SEQ ID NO 61
<211> LENGTH: 29
<212> TYPE: DNA
<213> ORGANISM: Artificial
<220> FEATURE:
<223> OTHER INFORMATION: primer

<400> SEQUENCE: 61
tttactatca tgtcatcatt tacaatagg                                   29

<210> SEQ ID NO 62
<211> LENGTH: 27
<212> TYPE: DNA
<213> ORGANISM: Artificial
<220> FEATURE:
<223> OTHER INFORMATION: primer

<400> SEQUENCE: 62
atttctgtta aatcctgaga catatcc                                        27

<210> SEQ ID NO 63
<211> LENGTH: 28
<212> TYPE: DNA
<213> ORGANISM: Artificial
<220> FEATURE:
<223> OTHER INFORMATION: primer

<400> SEQUENCE: 63
ttaagccaac tgaacttgac gctattgg                                       28

<210> SEQ ID NO 64
<211> LENGTH: 29
<212> TYPE: DNA
<213> ORGANISM: Artificial
<220> FEATURE:
<223> OTHER INFORMATION: primer

<400> SEQUENCE: 64
aaatctgttg tatgctgtaa aatatactc                                      29

<210> SEQ ID NO 65
<211> LENGTH: 28
<212> TYPE: DNA
<213> ORGANISM: Artificial
<220> FEATURE:
<223> OTHER INFORMATION: primer

<400> SEQUENCE: 65
tttacaatat tttttggtat cattgcag                                       28

<210> SEQ ID NO 66
<211> LENGTH: 28
<212> TYPE: DNA
<213> ORGANISM: Artificial
<220> FEATURE:
<223> OTHER INFORMATION: primer

<400> SEQUENCE: 66
aaaaactgcc aaatctccaa tctagtcc                                       28

<210> SEQ ID NO 67
<211> LENGTH: 24
<212> TYPE: DNA
<213> ORGANISM: Artificial
<220> FEATURE:
<223> OTHER INFORMATION: primer

<400> SEQUENCE: 67
aatatcgctt tggacacttg tagc                                           24

<210> SEQ ID NO 68
<211> LENGTH: 24
<212> TYPE: DNA
<213> ORGANISM: Artificial
<220> FEATURE:
<223> OTHER INFORMATION: primer -continued

```
<400> SEQUENCE: 68
ttccaattca acattgtact cacg                                            24

<210> SEQ ID NO 69
<211> LENGTH: 24
<212> TYPE: PRT
<213> ORGANISM: Artificial
<220> FEATURE:
<223> OTHER INFORMATION: fragment

<400> SEQUENCE: 69

Met Lys Thr Leu Lys Ile Phe Val Leu Phe Ser Leu Leu Ile Ala Ile
1               5                   10                  15

Leu Pro Tyr Phe Ala Gly Cys Leu
            20

<210> SEQ ID NO 70
<211> LENGTH: 23
<212> TYPE: PRT
<213> ORGANISM: Artificial
<220> FEATURE:
<223> OTHER INFORMATION: fragment

<400> SEQUENCE: 70

Lys Thr Leu Lys Ile Phe Val Leu Phe Ser Leu Leu Ile Ala Ile Leu
1               5                   10                  15

Pro Tyr Phe Ala Gly Cys Leu
            20

<210> SEQ ID NO 71
<211> LENGTH: 22
<212> TYPE: PRT
<213> ORGANISM: Artificial
<220> FEATURE:
<223> OTHER INFORMATION: fragment

<400> SEQUENCE: 71

Thr Leu Lys Ile Phe Val Leu Phe Ser Leu Leu Ile Ala Ile Leu Pro
1               5                   10                  15

Tyr Phe Ala Gly Cys Leu
            20

<210> SEQ ID NO 72
<211> LENGTH: 21
<212> TYPE: PRT
<213> ORGANISM: Artificial
<220> FEATURE:
<223> OTHER INFORMATION: fragment

<400> SEQUENCE: 72

Leu Lys Ile Phe Val Leu Phe Ser Leu Leu Ile Ala Ile Leu Pro Tyr
1               5                   10                  15

Phe Ala Gly Cys Leu
            20

<210> SEQ ID NO 73
<211> LENGTH: 20
<212> TYPE: PRT
<213> ORGANISM: Artificial
<220> FEATURE:
<223> OTHER INFORMATION: fragment

<400> SEQUENCE: 73

Lys Ile Phe Val Leu Phe Ser Leu Leu Ile Ala Ile Leu Pro Tyr Phe
```

```
                1               5                  10                 15
Ala Gly Cys Leu
            20

<210> SEQ ID NO 74
<211> LENGTH: 19
<212> TYPE: PRT
<213> ORGANISM: Artificial
<220> FEATURE:
<223> OTHER INFORMATION: fragment

<400> SEQUENCE: 74

Ile Phe Val Leu Phe Ser Leu Leu Ile Ala Ile Leu Pro Tyr Phe Ala
1               5                  10                 15

Gly Cys Leu

<210> SEQ ID NO 75
<211> LENGTH: 18
<212> TYPE: PRT
<213> ORGANISM: Artificial
<220> FEATURE:
<223> OTHER INFORMATION: fragment

<400> SEQUENCE: 75

Phe Val Leu Phe Ser Leu Leu Ile Ala Ile Leu Pro Tyr Phe Ala Gly
1               5                  10                 15

Cys Leu

<210> SEQ ID NO 76
<211> LENGTH: 17
<212> TYPE: PRT
<213> ORGANISM: Artificial
<220> FEATURE:
<223> OTHER INFORMATION: fragment

<400> SEQUENCE: 76

Val Leu Phe Ser Leu Leu Ile Ala Ile Leu Pro Tyr Phe Ala Gly Cys
1               5                  10                 15

Leu

<210> SEQ ID NO 77
<211> LENGTH: 16
<212> TYPE: PRT
<213> ORGANISM: Artificial
<220> FEATURE:
<223> OTHER INFORMATION: fragment

<400> SEQUENCE: 77

Leu Phe Ser Leu Leu Ile Ala Ile Leu Pro Tyr Phe Ala Gly Cys Leu
1               5                  10                 15

<210> SEQ ID NO 78
<211> LENGTH: 15
<212> TYPE: PRT
<213> ORGANISM: Artificial
<220> FEATURE:
<223> OTHER INFORMATION: fragment

<400> SEQUENCE: 78

Phe Ser Leu Leu Ile Ala Ile Leu Pro Tyr Phe Ala Gly Cys Leu
1               5                  10                 15

<210> SEQ ID NO 79
<211> LENGTH: 14
<212> TYPE: PRT
```

```
<213> ORGANISM: Artificial
<220> FEATURE:
<223> OTHER INFORMATION: fragment

<400> SEQUENCE: 79

Ser Leu Leu Ile Ala Ile Leu Pro Tyr Phe Ala Gly Cys Leu
1               5                   10

<210> SEQ ID NO 80
<211> LENGTH: 13
<212> TYPE: PRT
<213> ORGANISM: Artificial
<220> FEATURE:
<223> OTHER INFORMATION: fragment

<400> SEQUENCE: 80

Leu Leu Ile Ala Ile Leu Pro Tyr Phe Ala Gly Cys Leu
1               5                   10

<210> SEQ ID NO 81
<211> LENGTH: 12
<212> TYPE: PRT
<213> ORGANISM: Artificial
<220> FEATURE:
<223> OTHER INFORMATION: fragment

<400> SEQUENCE: 81

Leu Ile Ala Ile Leu Pro Tyr Phe Ala Gly Cys Leu
1               5                   10

<210> SEQ ID NO 82
<211> LENGTH: 11
<212> TYPE: PRT
<213> ORGANISM: Artificial
<220> FEATURE:
<223> OTHER INFORMATION: fragment

<400> SEQUENCE: 82

Ile Ala Ile Leu Pro Tyr Phe Ala Gly Cys Leu
1               5                   10

<210> SEQ ID NO 83
<211> LENGTH: 10
<212> TYPE: PRT
<213> ORGANISM: Artificial
<220> FEATURE:
<223> OTHER INFORMATION: fragment

<400> SEQUENCE: 83

Ala Ile Leu Pro Tyr Phe Ala Gly Cys Leu
1               5                   10

<210> SEQ ID NO 84
<211> LENGTH: 9
<212> TYPE: PRT
<213> ORGANISM: Artificial
<220> FEATURE:
<223> OTHER INFORMATION: fragment

<400> SEQUENCE: 84

Ile Leu Pro Tyr Phe Ala Gly Cys Leu
1               5

<210> SEQ ID NO 85
<211> LENGTH: 8
<212> TYPE: PRT
<213> ORGANISM: Artificial
<220> FEATURE:
```

```
<223> OTHER INFORMATION: fragment

<400> SEQUENCE: 85

Leu Pro Tyr Phe Ala Gly Cys Leu
1               5

<210> SEQ ID NO 86
<211> LENGTH: 7
<212> TYPE: PRT
<213> ORGANISM: Artificial
<220> FEATURE:
<223> OTHER INFORMATION: fragment

<400> SEQUENCE: 86

Pro Tyr Phe Ala Gly Cys Leu
1               5

<210> SEQ ID NO 87
<211> LENGTH: 6
<212> TYPE: PRT
<213> ORGANISM: Artificial
<220> FEATURE:
<223> OTHER INFORMATION: fragment

<400> SEQUENCE: 87

Tyr Phe Ala Gly Cys Leu
1               5

<210> SEQ ID NO 88
<211> LENGTH: 5
<212> TYPE: PRT
<213> ORGANISM: Artificial
<220> FEATURE:
<223> OTHER INFORMATION: fragment

<400> SEQUENCE: 88

Phe Ala Gly Cys Leu
1               5

<210> SEQ ID NO 89
<211> LENGTH: 4
<212> TYPE: PRT
<213> ORGANISM: Artificial
<220> FEATURE:
<223> OTHER INFORMATION: fragment

<400> SEQUENCE: 89

Ala Gly Cys Leu
1

<210> SEQ ID NO 90
<211> LENGTH: 7
<212> TYPE: PRT
<213> ORGANISM: Artificial
<220> FEATURE:
<223> OTHER INFORMATION: fragment

<400> SEQUENCE: 90

Ile Leu Pro Tyr Phe Ala Gly
1               5

<210> SEQ ID NO 91
<211> LENGTH: 6
<212> TYPE: PRT
<213> ORGANISM: Artificial
<220> FEATURE:
<223> OTHER INFORMATION: fragment
```

```
<400> SEQUENCE: 91

Pro Tyr Phe Ala Gly Cys
1               5

<210> SEQ ID NO 92
<211> LENGTH: 7
<212> TYPE: PRT
<213> ORGANISM: Artificial
<220> FEATURE:
<223> OTHER INFORMATION: fragment

<400> SEQUENCE: 92

Leu Pro Tyr Phe Ala Gly Cys
1               5

<210> SEQ ID NO 93
<211> LENGTH: 8
<212> TYPE: PRT
<213> ORGANISM: Artificial
<220> FEATURE:
<223> OTHER INFORMATION: fragment

<400> SEQUENCE: 93

Ile Leu Pro Tyr Phe Ala Gly Cys
1               5

<210> SEQ ID NO 94
<211> LENGTH: 9
<212> TYPE: PRT
<213> ORGANISM: Artificial
<220> FEATURE:
<223> OTHER INFORMATION: fragment

<400> SEQUENCE: 94

Ala Ile Leu Pro Tyr Phe Ala Gly Cys
1               5

<210> SEQ ID NO 95
<211> LENGTH: 5
<212> TYPE: PRT
<213> ORGANISM: Artificial
<220> FEATURE:
<223> OTHER INFORMATION: fragment

<400> SEQUENCE: 95

Pro Tyr Phe Ala Gly
1               5

<210> SEQ ID NO 96
<211> LENGTH: 24
<212> TYPE: PRT
<213> ORGANISM: Artificial
<220> FEATURE:
<223> OTHER INFORMATION: fragment

<400> SEQUENCE: 96

Met Lys Thr Leu Lys Ile Phe Val Leu Phe Ser Leu Leu Ile Pro Ile
1               5                   10                  15

Leu Pro Tyr Phe Ala Gly Cys Leu
            20

<210> SEQ ID NO 97
<211> LENGTH: 23
<212> TYPE: PRT
<213> ORGANISM: Artificial
<220> FEATURE:
<223> OTHER INFORMATION: fragment
```

<400> SEQUENCE: 97

Lys Thr Leu Lys Ile Phe Val Leu Phe Ser Leu Leu Ile Pro Ile Leu
1               5                   10                  15

Pro Tyr Phe Ala Gly Cys Leu
            20

<210> SEQ ID NO 98
<211> LENGTH: 22
<212> TYPE: PRT
<213> ORGANISM: Artificial
<220> FEATURE:
<223> OTHER INFORMATION: fragment

<400> SEQUENCE: 98

Thr Leu Lys Ile Phe Val Leu Phe Ser Leu Leu Ile Pro Ile Leu Pro
1               5                   10                  15

Tyr Phe Ala Gly Cys Leu
            20

<210> SEQ ID NO 99
<211> LENGTH: 21
<212> TYPE: PRT
<213> ORGANISM: Artificial
<220> FEATURE:
<223> OTHER INFORMATION: fragment

<400> SEQUENCE: 99

Leu Lys Ile Phe Val Leu Phe Ser Leu Leu Ile Pro Ile Leu Pro Tyr
1               5                   10                  15

Phe Ala Gly Cys Leu
            20

<210> SEQ ID NO 100
<211> LENGTH: 20
<212> TYPE: PRT
<213> ORGANISM: Artificial
<220> FEATURE:
<223> OTHER INFORMATION: fragment

<400> SEQUENCE: 100

Lys Ile Phe Val Leu Phe Ser Leu Leu Ile Pro Ile Leu Pro Tyr Phe
1               5                   10                  15

Ala Gly Cys Leu
            20

<210> SEQ ID NO 101
<211> LENGTH: 19
<212> TYPE: PRT
<213> ORGANISM: Artificial
<220> FEATURE:
<223> OTHER INFORMATION: fragment

<400> SEQUENCE: 101

Ile Phe Val Leu Phe Ser Leu Leu Ile Pro Ile Leu Pro Tyr Phe Ala
1               5                   10                  15

Gly Cys Leu

<210> SEQ ID NO 102
<211> LENGTH: 18
<212> TYPE: PRT
<213> ORGANISM: Artificial
<220> FEATURE:
<223> OTHER INFORMATION: fragment -continued

```
<400> SEQUENCE: 102

Phe Val Leu Phe Ser Leu Leu Ile Pro Ile Leu Pro Tyr Phe Ala Gly
1               5                   10                  15

Cys Leu

<210> SEQ ID NO 103
<211> LENGTH: 17
<212> TYPE: PRT
<213> ORGANISM: Artificial
<220> FEATURE:
<223> OTHER INFORMATION: fragment

<400> SEQUENCE: 103

Val Leu Phe Ser Leu Leu Ile Pro Ile Leu Pro Tyr Phe Ala Gly Cys
1               5                   10                  15

Leu

<210> SEQ ID NO 104
<211> LENGTH: 16
<212> TYPE: PRT
<213> ORGANISM: Artificial
<220> FEATURE:
<223> OTHER INFORMATION: fragment

<400> SEQUENCE: 104

Leu Phe Ser Leu Leu Ile Pro Ile Leu Pro Tyr Phe Ala Gly Cys Leu
1               5                   10                  15

<210> SEQ ID NO 105
<211> LENGTH: 15
<212> TYPE: PRT
<213> ORGANISM: Artificial
<220> FEATURE:
<223> OTHER INFORMATION: fragment

<400> SEQUENCE: 105

Phe Ser Leu Leu Ile Pro Ile Leu Pro Tyr Phe Ala Gly Cys Leu
1               5                   10                  15

<210> SEQ ID NO 106
<211> LENGTH: 14
<212> TYPE: PRT
<213> ORGANISM: Artificial
<220> FEATURE:
<223> OTHER INFORMATION: fragment

<400> SEQUENCE: 106

Ser Leu Leu Ile Pro Ile Leu Pro Tyr Phe Ala Gly Cys Leu
1               5                   10

<210> SEQ ID NO 107
<211> LENGTH: 13
<212> TYPE: PRT
<213> ORGANISM: Artificial
<220> FEATURE:
<223> OTHER INFORMATION: fragment

<400> SEQUENCE: 107

Leu Leu Ile Pro Ile Leu Pro Tyr Phe Ala Gly Cys Leu
1               5                   10

<210> SEQ ID NO 108
<211> LENGTH: 12
<212> TYPE: PRT
<213> ORGANISM: Artificial
<220> FEATURE:
```

```
<223> OTHER INFORMATION: fragment

<400> SEQUENCE: 108

Leu Ile Pro Ile Leu Pro Tyr Phe Ala Gly Cys Leu
1               5                   10

<210> SEQ ID NO 109
<211> LENGTH: 11
<212> TYPE: PRT
<213> ORGANISM: Artificial
<220> FEATURE:
<223> OTHER INFORMATION: fragment

<400> SEQUENCE: 109

Ile Pro Ile Leu Pro Tyr Phe Ala Gly Cys Leu
1               5                   10

<210> SEQ ID NO 110
<211> LENGTH: 10
<212> TYPE: PRT
<213> ORGANISM: Artificial
<220> FEATURE:
<223> OTHER INFORMATION: fragment

<400> SEQUENCE: 110

Pro Ile Leu Pro Tyr Phe Ala Gly Cys Leu
1               5                   10

<210> SEQ ID NO 111
<211> LENGTH: 24
<212> TYPE: PRT
<213> ORGANISM: Artificial
<220> FEATURE:
<223> OTHER INFORMATION: fragment

<400> SEQUENCE: 111

Met Lys Lys Leu Lys Leu Phe Thr Leu Phe Ser Leu Leu Ile Thr Ile
1               5                   10                  15

Leu Pro Tyr Phe Thr Gly Cys Leu
            20

<210> SEQ ID NO 112
<211> LENGTH: 23
<212> TYPE: PRT
<213> ORGANISM: Artificial
<220> FEATURE:
<223> OTHER INFORMATION: fragment

<400> SEQUENCE: 112

Lys Lys Leu Lys Leu Phe Thr Leu Phe Ser Leu Leu Ile Thr Ile Leu
1               5                   10                  15

Pro Tyr Phe Thr Gly Cys Leu
            20

<210> SEQ ID NO 113
<211> LENGTH: 22
<212> TYPE: PRT
<213> ORGANISM: Artificial
<220> FEATURE:
<223> OTHER INFORMATION: fragment

<400> SEQUENCE: 113

Lys Leu Lys Leu Phe Thr Leu Phe Ser Leu Leu Ile Thr Ile Leu Pro
1               5                   10                  15

Tyr Phe Thr Gly Cys Leu
            20
```

```
<210> SEQ ID NO 114
<211> LENGTH: 21
<212> TYPE: PRT
<213> ORGANISM: Artificial
<220> FEATURE:
<223> OTHER INFORMATION: fragment

<400> SEQUENCE: 114

Leu Lys Leu Phe Thr Leu Phe Ser Leu Leu Ile Thr Ile Leu Pro Tyr
1               5                   10                  15

Phe Thr Gly Cys Leu
            20

<210> SEQ ID NO 115
<211> LENGTH: 20
<212> TYPE: PRT
<213> ORGANISM: Artificial
<220> FEATURE:
<223> OTHER INFORMATION: fragment

<400> SEQUENCE: 115

Lys Leu Phe Thr Leu Phe Ser Leu Leu Ile Thr Ile Leu Pro Tyr Phe
1               5                   10                  15

Thr Gly Cys Leu
            20

<210> SEQ ID NO 116
<211> LENGTH: 19
<212> TYPE: PRT
<213> ORGANISM: Artificial
<220> FEATURE:
<223> OTHER INFORMATION: fragment

<400> SEQUENCE: 116

Leu Phe Thr Leu Phe Ser Leu Leu Ile Thr Ile Leu Pro Tyr Phe Thr
1               5                   10                  15

Gly Cys Leu

<210> SEQ ID NO 117
<211> LENGTH: 18
<212> TYPE: PRT
<213> ORGANISM: Artificial
<220> FEATURE:
<223> OTHER INFORMATION: fragment

<400> SEQUENCE: 117

Phe Thr Leu Phe Ser Leu Leu Ile Thr Ile Leu Pro Tyr Phe Thr Gly
1               5                   10                  15

Cys Leu

<210> SEQ ID NO 118
<211> LENGTH: 17
<212> TYPE: PRT
<213> ORGANISM: Artificial
<220> FEATURE:
<223> OTHER INFORMATION: fragment

<400> SEQUENCE: 118

Thr Leu Phe Ser Leu Leu Ile Thr Ile Leu Pro Tyr Phe Thr Gly Cys
1               5                   10                  15

Leu

<210> SEQ ID NO 119
```

```
<211> LENGTH: 16
<212> TYPE: PRT
<213> ORGANISM: Artificial
<220> FEATURE:
<223> OTHER INFORMATION: fragment

<400> SEQUENCE: 119

Leu Phe Ser Leu Leu Ile Thr Ile Leu Pro Tyr Phe Thr Gly Cys Leu
1               5                   10                  15

<210> SEQ ID NO 120
<211> LENGTH: 15
<212> TYPE: PRT
<213> ORGANISM: Artificial
<220> FEATURE:
<223> OTHER INFORMATION: fragment

<400> SEQUENCE: 120

Phe Ser Leu Leu Ile Thr Ile Leu Pro Tyr Phe Thr Gly Cys Leu
1               5                   10                  15

<210> SEQ ID NO 121
<211> LENGTH: 14
<212> TYPE: PRT
<213> ORGANISM: Artificial
<220> FEATURE:
<223> OTHER INFORMATION: fragment

<400> SEQUENCE: 121

Ser Leu Leu Ile Thr Ile Leu Pro Tyr Phe Thr Gly Cys Leu
1               5                   10

<210> SEQ ID NO 122
<211> LENGTH: 13
<212> TYPE: PRT
<213> ORGANISM: Artificial
<220> FEATURE:
<223> OTHER INFORMATION: fragment

<400> SEQUENCE: 122

Leu Leu Ile Thr Ile Leu Pro Tyr Phe Thr Gly Cys Leu
1               5                   10

<210> SEQ ID NO 123
<211> LENGTH: 12
<212> TYPE: PRT
<213> ORGANISM: Artificial
<220> FEATURE:
<223> OTHER INFORMATION: fragment

<400> SEQUENCE: 123

Leu Ile Thr Ile Leu Pro Tyr Phe Thr Gly Cys Leu
1               5                   10

<210> SEQ ID NO 124
<211> LENGTH: 11
<212> TYPE: PRT
<213> ORGANISM: Artificial
<220> FEATURE:
<223> OTHER INFORMATION: fragment

<400> SEQUENCE: 124

Ile Thr Ile Leu Pro Tyr Phe Thr Gly Cys Leu
1               5                   10

<210> SEQ ID NO 125
<211> LENGTH: 10
<212> TYPE: PRT
```

```
<213> ORGANISM: Artificial
<220> FEATURE:
<223> OTHER INFORMATION: fragment

<400> SEQUENCE: 125

Thr Ile Leu Pro Tyr Phe Thr Gly Cys Leu
1               5                   10

<210> SEQ ID NO 126
<211> LENGTH: 9
<212> TYPE: PRT
<213> ORGANISM: Artificial
<220> FEATURE:
<223> OTHER INFORMATION: fragment

<400> SEQUENCE: 126

Ile Leu Pro Tyr Phe Thr Gly Cys Leu
1               5

<210> SEQ ID NO 127
<211> LENGTH: 8
<212> TYPE: PRT
<213> ORGANISM: Artificial
<220> FEATURE:
<223> OTHER INFORMATION: fragment

<400> SEQUENCE: 127

Leu Pro Tyr Phe Thr Gly Cys Leu
1               5

<210> SEQ ID NO 128
<211> LENGTH: 7
<212> TYPE: PRT
<213> ORGANISM: Artificial
<220> FEATURE:
<223> OTHER INFORMATION: fragment

<400> SEQUENCE: 128

Pro Tyr Phe Thr Gly Cys Leu
1               5

<210> SEQ ID NO 129
<211> LENGTH: 6
<212> TYPE: PRT
<213> ORGANISM: Artificial
<220> FEATURE:
<223> OTHER INFORMATION: fragment

<400> SEQUENCE: 129

Tyr Phe Thr Gly Cys Leu
1               5

<210> SEQ ID NO 130
<211> LENGTH: 5
<212> TYPE: PRT
<213> ORGANISM: Artificial
<220> FEATURE:
<223> OTHER INFORMATION: fragment

<400> SEQUENCE: 130

Phe Thr Gly Cys Leu
1               5

<210> SEQ ID NO 131
<211> LENGTH: 4
<212> TYPE: PRT
<213> ORGANISM: Artificial
<220> FEATURE:
```

```
<223> OTHER INFORMATION: fragment

<400> SEQUENCE: 131

Thr Gly Cys Leu
1
```